(12) United States Patent
Macoviak et al.

(10) Patent No.: US 6,395,014 B1
(45) Date of Patent: May 28, 2002

(54) CEREBRAL EMBOLIC PROTECTION ASSEMBLY AND ASSOCIATED METHODS

(76) Inventors: John A. Macoviak; Wilfred J. Samson, both of 10161 Bubb Rd., Cupertino, CA (US) 95014

(*) Notice: Subject to any disclaimer, the term of this patent is extended or adjusted under 35 U.S.C. 154(b) by 0 days.

(21) Appl. No.: 09/447,458

(22) Filed: Nov. 22, 1999

Related U.S. Application Data

(63) Continuation-in-part of application No. 09/378,676, filed on Aug. 20, 1999, which is a continuation-in-part of application No. 09/158,405, filed on Sep. 22, 1998.
(60) Provisional application No. 60/060,117, filed on Sep. 26, 1997, and provisional application No. 60/116,836, filed on Jan. 22, 1999.

(51) Int. Cl.[7] ............................................. A61M 29/00
(52) U.S. Cl. ....................................... 606/200; 606/194
(58) Field of Search ......................... 606/113.151, 198, 606/200, 170, 194; 623/1.36; 604/96.01

(56) References Cited

U.S. PATENT DOCUMENTS

| | | | | |
|---|---|---|---|---|
| 4,723,549 A | * | 2/1988 | Wholey et al. | 606/194 |
| 5,368,555 A | | 11/1994 | Sussman et al. | |
| 5,662,671 A | * | 9/1997 | Barbut et al. | 606/170 |
| 5,814,064 A | * | 9/1998 | Daniel et al. | 606/200 |
| 6,258,120 B1 | | 7/2001 | McKenzie et al. | |

OTHER PUBLICATIONS

David P. Bichell, MD, et al., Axilloaxillary Cardiopulmonary Bypass: A Practical Alternative to Femorofemoral Bypass. ©1997 by The Society of Thoracic Surgeons Published by Elsevier Science Inc., pp. 702–705.

Joseph F. Sabik, MD, et al., Axillary Artery: An Alternative Site of Arterial Cannulation for Patients with Extensive Aortic and Peripheral Vascular Disease, ©1995 by Mosby–Year Book, Inc., The Journal of Thoracic and Cardiovascular Surgery , pp. 886–891.

Nicholas T. Kouchoukos, et al., Perfusion for Thoracic Aortic Surgery, Section V. Clinical Application and Management of CPB, pp. 636–654.

* cited by examiner

*Primary Examiner*—David O. Reip
*Assistant Examiner*—Julian W. Woo
(74) *Attorney, Agent, or Firm*—Fulwider Patton Lee & Utecht

(57) ABSTRACT

The present invention is related to cerebral embolic protection assemblies (CEPA) to be used during a medical procedure to help redirect or catch emboli before it is pumped into the cerebral circulation. A variety of CEPA's are disclosed including a perfusion filter catheters and fluid flow dividers for capturing and redirecting potential emboli within the aorta during heart surgery and cardiopulmonary bypass. The catheter devices may further include one or more additional or auxiliary flow control members. Furthermore, oxygenated blood is perfused through a perfusion lumen in the catheter. The present invention describes devices that are capable of capturing and/or redirected emboli away from the cerebral circulation. The devices are configured for percutaneous, intercostal, lateral or central insertion with attendant administration of cardiopulmonary bypass and cardioplegic arrest with protection from undesirable embolic events.

51 Claims, 13 Drawing Sheets

CEREBRAL EMBOLIC PROTECTION ASSEMBLY AND ASSOCIATED METHODS

CROSS REFERENCE TO OTHER APPLICATIONS

This application is a continuation-in-part of application Ser. No.: 09/158,405 filed Sep. 22, 1998, which claims the benefit of U.S. Provisional Application No. 60/060,117 filed Sep. 26, 1997, which are hereby incorporated by reference in their entirety for all purposes. This application is also a continuation-in-part of application Ser. No.: 09/378,676 filed Aug. 20, 1999, which claims the benefit of U.S. Provisional Application No. 60/116,836 filed Jan. 22, 1999, which are hereby incorporated by reference in their entirety for all purposes.

FIELD OF THE INVENTION

The present invention relates generally to a catheter or cannula for infusion of oxygenated blood or other fluids into a patient for cardiopulmonary support and cerebral protection. More particularly, it relates to an arterial perfusion catheter with a deployable cerebral embolic protection assembly (CEPA) for protecting a patient from adverse effects due to emboli that are dislodged during cardiopulmonary bypass.

BACKGROUND

Over the past decades tremendous advances have been made in the area of heart surgery, including such life saving surgical procedures as coronary artery bypass grafting (CABG) and cardiac valve repair or replacement surgery. Typically, in order to gain access to the heart a median sternotomy is performed, which creates an open surgical field, conducive for the placement of cannulae and direct visualization for performing the required procedure. Heart activity generally ceases for some period of time, and cardiopulmonary support is provided by diverting blood through an extracorporeal circuit to maintain sufficient oxygenated blood flow to the body and brain while the heart is arrested. Cardiopulmonary bypass (CPB) is a technology that has made these advances possible.

Recently, however, there has been a growing awareness within the medical community as well as the patient population concerning the adverse affects associated with heart surgery, the large amount of trauma associated with median sternotomies, as well as well the physiological reactions associated with cardiopulmonary bypass. Chief among these concerns is the potential for stroke or neurologic deficit.

Clinical research has indicated that one of the primary causes of stroke or neurologic deficit is cerebral embolization. Emboli vary in size as well as physical properties and their sources vary. However, embolic materials include atherosclerotic plaques or calcific plaques residing within the ascending aorta or cardiac valves and thrombus or clots from within the chambers of the heart. Emboli may also be dislodged during surgical manipulation of the heart, the ascending aorta, cross-clamping, aortic cannulation or due to high velocity jetting (sometimes called the "sandblasting effect") from the aortic perfusion cannula. In addition, air can enter the heart chambers or the blood stream during surgery through open incisions or through the aortic perfusion cannula. As blood is pumped to the brain, either through the extracorporeal circuit or by the beating heart in an off-pump minimally invasive procedure, transient or mobile emboli can become lodged in the brain causing a stroke or other neurologic deficit. Clinical studies have shown a correlation between the number and size of emboli passing through the carotid arteries and the frequency and severity of neurologic damage. At least one study has found that frank strokes seem to be associated with macroemboli larger than approximately 100 micrometers in size, whereas more subtle neurologic deficits seem to be associated with multiple microemboli smaller than approximately 100 micrometers in size. In order to improve the outcome of cardiac surgery and to avoid adverse neurological effects it would be very beneficial to eliminate or reduce the potential of such cerebral embolic events.

Therefore, what has been needed and heretofore unavailable, is a catheter device for standard open chest surgery and for use in minimally invasive medical procedures that is simple and relatively inexpensive. One which is capable of isolating the circulation of the arch vessels, while still allowing the heart to perform the function of perfusing the body or alternatively one that can be used in conjunction with an extracorporeal circuit. The present invention solves these problems as well as others.

The terms downstream and upstream, when used herein in relation to the patient's vasculature, refer to the direction of blood flow and the direction opposite that of blood flow, respectively. In the arterial system, downstream refers to the direction further from the heart, while upstream refers to the direction closer to the heart. The terms proximal and distal, when used herein in relation to instruments used in the procedure, refer to directions closer to and farther away from the operator performing the procedure. Since the present invention is not limited to peripheral or central approaches, the device should not be narrowly construed when using the terms proximal or distal since device features may be slightly altered relative to the anatomical features and the device position relative thereto.

SUMMARY OF THE INVENTION

In keeping with the foregoing discussion, the present invention takes the form of a catheter or cannula having a cerebral embolic protection assembly (CEPA) mounted on an elongated tubular catheter shaft. The elongated tubular catheter shaft is adapted for introduction into a patient's ascending aorta either by a peripheral arterial approach or by a direct aortic puncture. The CEPA has an undeployed state where it is compressed or wrapped tightly around the catheter shaft and a deployed state where it expands to the size of the aortic lumen. The CEPA assembly can be passively or actively deployed. Various mechanisms are disclosed for both passive and active deployment.

Radiopaque markers and/or sonoreflective markers may be located on the catheter and/or CEPA. Preferably, a perfusion lumen extends through the elongated tubular catheter shaft to one or more perfusion ports upstream and/or downstream of the CEPA. Oxygenated blood is perfused through the perfusion lumen, through the beating heat or a combination of both. Any embolic materials that might be dislodged are captured or rerouted by the CEPA.

Embodiments are also described that combine the CEPA with an aortic occlusion device, which may be a toroidal balloon, an expandable balloon or a selectively deployable external catheter flow control valve. The combined device allows percutaneous transluminal administration of cardiopulmonary bypass and cardioplegic arrest with protection from undesirable embolic events, as well as differential perfusion.

In use, the CEPA is introduced into the patient's aorta, either by a peripheral arterial approach or by direct aortic puncture, with the CEPA in a collapsed state. The CEPA is advanced across the aortic arch and into the arch and ascending aorta. When a portion of the CEPA is positioned in the ascending aorta between the aortic valve and the brachiocephalic artery, the CEPA is either actively or passively deployed. The position of the catheter and the deployment state of the CEPA may be monitored using fluoroscopy, ultrasound, transesophageal echography (TEE) or aortic transillumination using visible, infrared or near infrared light. Once the CEPA is deployed, oxygenated blood may be infused into the aorta through the perfusion lumen or alternatively the beating heart may supply all the blood or a combination of both. Any potential emboli are captured or rerouted by the CEPA and are thereby prevented from entering the neurovasculature. After use, the CEPA is returned to the collapsed position and the catheter is withdrawn from the patient.

Methods according to the present invention are described using the aortic catheter for occluding and compartmentalizing or partitioning the patient's aortic lumen and for performing selective filtered aortic perfusion.

BRIEF DESCRIPTION OF THE DRAWINGS

FIG. 1 is a cutaway perspective view of the perfusion filter catheter deployed within the aorta via femoral artery access. FIG. 2 shows the distal end of the catheter with the embolic filter assembly in a deployed state. FIG. 3 shows the distal end of the catheter with the embolic filter assembly in a collapsed state for insertion or withdrawal of the device from the patient.

DETAILED DESCRIPTION

Figure 1:
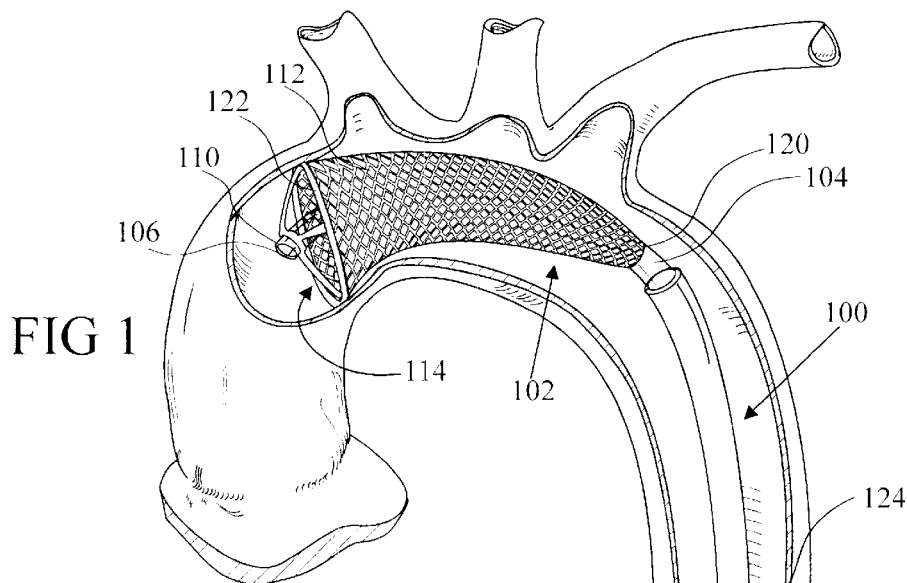
FIGS. 1–3 show a perfusion filter catheter configured for retrograde deployment via a peripheral arterial access point.
Figure 2:
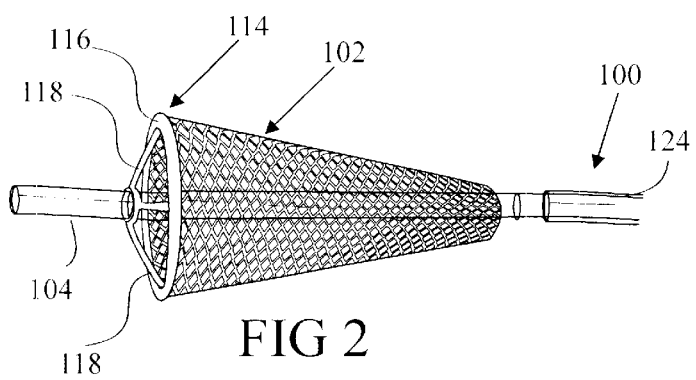
Figure 3:
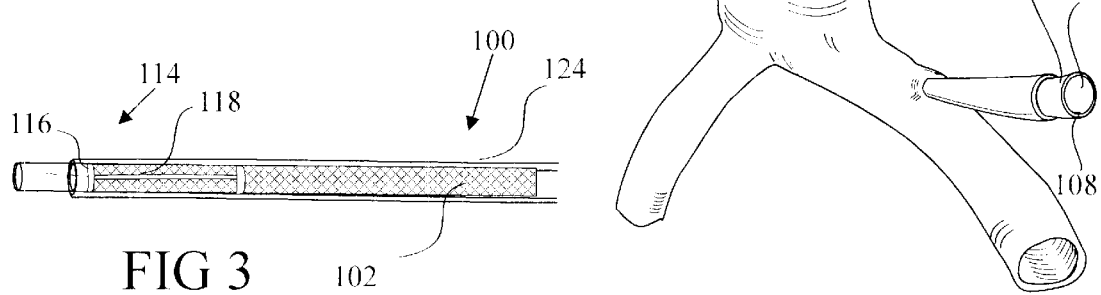

FIGS. 1–3 illustrate a first embodiment of the present invention having a CEPA in the form of a perfusion filter catheter. FIGS. 1–3 show a perfusion filter catheter 100 according to the present invention configured for retrograde deployment via a peripheral arterial access point. FIG. 1 is a cutaway perspective view of the perfusion filter catheter 100 deployed within the aorta of a patient via femoral artery access. FIG. 2 shows the distal end of the catheter 100 with the embolic filter assembly 102 in a deployed state. FIG. 3 shows the distal end of the catheter 100 with the embolic filter assembly 102' in a collapsed state for insertion or withdrawal of the device from the patient.

Referring now to FIG. 1, the catheter 100 includes a cannula shaft having a tubular body 104 and a CEPA in the form of a filter assembly 102. The tubular body has a proximal end 108 and distal end 110 and is preferably extruded from a flexible thermoplastic material or a thermoplastic elastomer. Suitable materials for the tubular body 104 include, but are not limited to, polyvinylchloride, polyurethane, polyethylene, polypropylene, polyamides (nylons), and alloys or copolymers thereof, as well as braided, coiled or counterwound wire or filament reinforced composites. The tubular body 104 may have a single lumen or multilumen construction. In the exemplary embodiment shown, the catheter 100 has a single perfusion lumen 106 extending from the proximal end 108 to the distal end 110 of the catheter shaft 104. The perfusion lumen 106 is open at the distal end 110 of the catheter shaft 104. The distal end 110 of the catheter shaft 104 may have a simple beveled or rounded distal edge, as shown, or it may include additional side ports or a flow diffuser to reduce jetting when oxygenated blood is infused through the perfusion lumen 106. The proximal end 108 of the elongated tubular catheter shaft 104 is adapted for connecting the perfusion lumen 106 to a cardiopulmonary bypass pump or other source of oxygenated blood using standard barb connectors or other connectors, such as a standard luer fitting (not shown) and suitable medical tubing. Preferably, the catheter shaft 104 is made with thin walled construction to maximize the internal diameter and therefore the flow rate of the perfusion lumen 106 for a given outside diameter and length of the catheter shaft 104. Thin walled construction also allows the outside diameter of the catheter shaft 104 to be minimized in order to reduce the invasiveness of the procedure and to reduce trauma at the insertion site. The perfusion lumen 106 should be configured to allow sufficient blood flow to preserve organ function without hemolysis or other damage to the blood. For standard cardiopulmonary support techniques, a catheter shaft 104 of 18–24 French size (6–8 mm outside diameter) is sufficient to deliver the requisite 3–4 liters of oxygenated blood to preserve organ function. For low flow cardiopulmonary support techniques, such as described in commonly owned, copending patent application Ser. No. 60/084,835, filed May 8, 1998 and its corresponding utility application Ser. No. 09/306,555 filed on May 6, 1999 which are hereby incorporated by reference, the size of the catheter shaft 104 can be reduced to 9–18 French size (3–6 mm outside diameter) for delivering 0.5–3 liters of oxygenated blood to preserve organ function. The catheter shaft 104 should have a length sufficient to reach from the arterial access point where it is inserted to the ascending aorta of the patient. For femoral artery deployment, the catheter shaft 104 preferably has a length from approximately 80–120 cm.

A deployable embolic filter assembly 102 is located just proximal to the distal end 110 of the catheter shaft 104. The embolic filter assembly 102 includes a filter screen 112 made of a fine mesh material. In this exemplary embodiment and each of the other embodiments described below, the fine mesh material of the filter screen 112 may be a woven or knitted fabric, such as Dacron polyester or nylon mesh, or other textile fabrics, or it may be a nonwoven fabric, such as a spun bonded polyolefin or expanded polytetrafluoroethylene or other nonwoven materials. The fine mesh material of the filter screen 112 may be woven, knitted or otherwise formed from monofilament or multifilament fibers. The fine mesh material of the filter screen 112 may also be a fine wire mesh or a combination of wire and textile fibers. Alternatively, the fine mesh material of the filter screen 112 may be an open cell foam material. The fine mesh material of the filter screen 112 must be nontoxic and hemocompatible, that is, non-thrombogenic and non-hemolytic. Preferably, the fine mesh material of the filter screen 112 has a high percentage of open space, with a uniform pore size. The pore size of the filter screen 112 can be chosen to capture macroemboli only or to capture macroemboli and microemboli. In most cases the pore size of the filter screen 112 will preferably be in the range of 1–200 micrometers. For capturing macroemboli only, the pore size of the filter screen 112 will preferably be in the range of 50–200 micrometers, more preferably in the range of 80–100 micrometers. For capturing macroemboli and microemboli, the pore size of the filter screen 112 will preferably be in the range of 1–100 micrometers, more preferably in the range of 5–20 micrometers. In other applications, such as for treating thromboembolic disease, a larger pore size, e.g. up to 1000 micrometers (1 mm) or larger, would also be useful. In some embodiments, a combination of filter materials having different pore sizes may be used.

Alternatively or additionally the material of the filter screen in each embodiment of the filter catheter may be made of or coated with an adherent material or substance to capture or hold embolic debris which comes into contact with the filter screen within the embolic filter assembly. Suitable adherent materials include, but are not limited to, known biocompatible adhesives and bioadhesive materials or substances, which are hemocompatible and non-thrombogenic. Such materials are known to those having ordinary skill in the art and are described in, among other references, U.S. Pat. Nos. 4,768,523, 5,055,046, 5,066,709, 5,197,973, 5,225,196, 5,374,431, 5,578,310, 5,645,062, 5,648,167, 5,651,982, and 5,665,477. In one particularly preferred embodiment, only the upstream side of the elements of the filter screen are coated with the adherent material to positively capture the embolic debris which comes in contact with the upstream side of the filter screen after entering the filter assembly. Other bioactive substances, for example, heparin or thrombolytic agents, may be impregnated into or coated on the surface of the filter screen material or incorporated into an adhesive coating.

The embolic filter assembly 102 is movable between a collapsed state, as shown in FIG. 3, and an expanded or deployed state, as shown in FIGS. 1 and 2. The filter screen 112 may be attached directly to the catheter shaft 104 and it may constitute the entire embolic filter assembly 102, particularly if the filter screen 112 is made of a resilient or semirigid fabric that has enough body to be self-supporting in the deployed state. Generally, however, the embolic filter assembly 102 will also include a filter support structure 114, particularly if a highly flexible or flaccid material is used for the filter screen 112. The filter support structure 114 attaches and supports the filter screen 112 on the catheter shaft 104. In the illustrative embodiment of FIGS. 1–3, the filter support structure 114 is constructed with an outer hoop 116 and a plurality of struts 118 which extend approximately radially from a ring-shaped hub 126 that is mounted on the catheter shaft 104. In this case four struts 118 are shown, however, two, three or more struts 118 may be used. The open distal end 122 of the filter screen 112 is attached to the outer hoop 116 and the proximal end 120 of the filter screen 112 is sealingly attached to the catheter shaft 104. When the embolic filter assembly 102 is deployed, the outer hoop 116 of the filter support structure 114 holds the open distal end 122 of the filter screen 112 against the inner wall of the aorta, as shown in FIG. 1. To accommodate most normal adult aortas, the outer hoop 116 of the filter support structure 114 and the distal end 122 of the filter screen 112 have a diameter of approximately 2.5 to 4 cm, plus or minus 0.5 cm. Larger and smaller diameter filter support structures 114 may be made to accommodate patients with distended or Marfan syndrome aortas or for pediatric patients.

The embolic filter assembly 102 may be deployed by a passive means or by an active means. Passive means for deploying the embolic filter assembly 102 could include using the elastic memory of the filter screen 112 and/or the filter support structure 114 to deploy the embolic filter assembly 102, and/or using pressure from the blood flow in the aorta to deploy the embolic filter assembly 102. By contrast, active means for deploying the embolic filter assembly 102 could include one or more actuation members within the catheter shaft 104 for mechanically actuating the filter support structure 114 to deploy the embolic filter assembly 102 from the proximal end 108 of the catheter 100. Shape memory materials may also be used as actuation members for deploying the embolic filter assembly 102. Alternatively, active means for deploying the embolic filter assembly 102 could include one or more lumens within the catheter shaft 104 for hydraulically actuating the filter support structure 114 to deploy the embolic filter assembly 102. Passive means may be used to augment the action of the active deployment means. As shown in FIG. 3, an outer tube 124 may be provided to cover the embolic filter assembly 102 when it is in the collapsed state in order to create a smooth outer surface for insertion and withdrawal of the catheter 100 and to prevent premature deployment of the embolic filter assembly 102, particularly if passive deployment means are used.

The perfusion filter catheter 100 is prepared for use by folding or compressing the embolic filter assembly 102' into a collapsed state within the outer tube 124, as shown in FIG. 3. The distal end 110 of the catheter 100 is inserted into the aorta in a retrograde fashion. Preferably, this is done through a peripheral arterial access, such as the femoral artery or subclavian artery, using the Seldinger technique or an arterial cutdown. Alternatively, the catheter 100 may be introduced directly through an incision into the descending aorta after the aorta has been surgically exposed. The embolic filter assembly 102 is advanced up the descending aorta and across the aortic arch while in the collapsed state. The position of the catheter 100 may be monitored using fluoroscopy or ultrasound, such as transesophageal echography (TEE). Appropriate markers, which may include radiopaque markers and/or sonoreflective markers, may be located on the distal end 110 of the catheter 100 and/or the embolic filter assembly 102 to enhance imaging and to show the position of the catheter 100 and the deployment state of the embolic filter assembly 102. When the distal end 110 of the catheter 100 is positioned in the ascending aorta between the aortic valve and the brachiocephalic artery, the outer tube 124 is withdrawn and the embolic filter assembly 102 is deployed, as shown in FIG. 1. Optionally, a distal portion of the catheter shaft 104 may be precurved to match the curvature of the aortic arch to aid in placement and stabilization of the catheter 100 and the embolic filter assembly 102 within the aorta. Once the embolic filter assembly 102 is deployed, oxygenated blood may be infused through the perfusion lumen 106 to augment cardiac output of the beating heart or to establish cardiopulmonary bypass so that the heart can be arrested. Any potential emboli are captured by the filter screen 112 and prevented from entering the neurovasculature or other branches downstream. After use, the embolic filter assembly 102 is returned to the collapsed position and the catheter 100 is withdrawn from the patient.

Preferably, the embolic filter assembly 102 is configured so that, when it is in the deployed state, at least a majority of the filter screen 112 is held away from the aortic walls so that flow through the pores of the filter screen 112 is not occluded by contact with the aortic wall. In addition, this also assures that blood flow into the side branches of the aorta will not be obstructed by the filter screen 112. In this way, each side branch of the aorta will receive the benefit of flow through the full surface area of the filter screen 112 so that blood flow is not restricted by the area of the ostium of each side branch. In the illustrative embodiment of FIGS. 1–3, the filter screen 112 has a roughly conical shape with an open distal end 122. The conical shape holds the fine mesh material of the filter screen 112 away from the aortic walls and away from the ostia of the side branches so that blood can flow freely through the pores of the filter screen 112.

Figure 4:
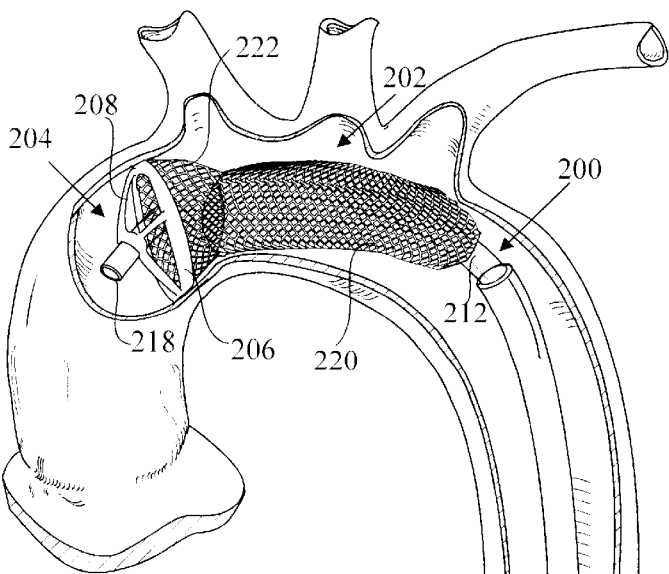
FIGS. 4–6 show a method of actively deploying an embolic filter assembly with an inflatable filter support structure.
Figure 5:
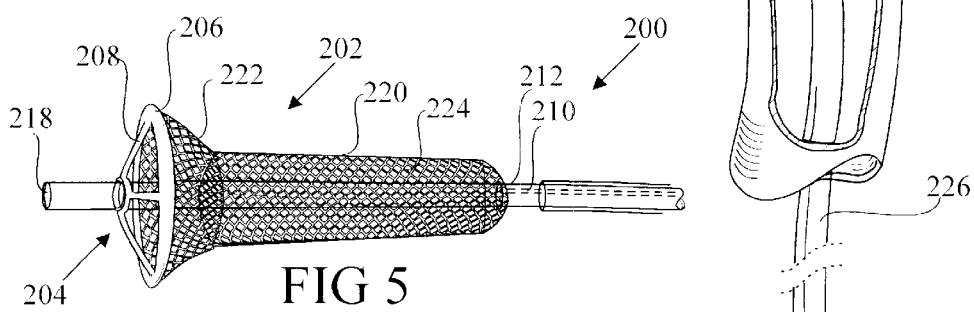
Figure 6:
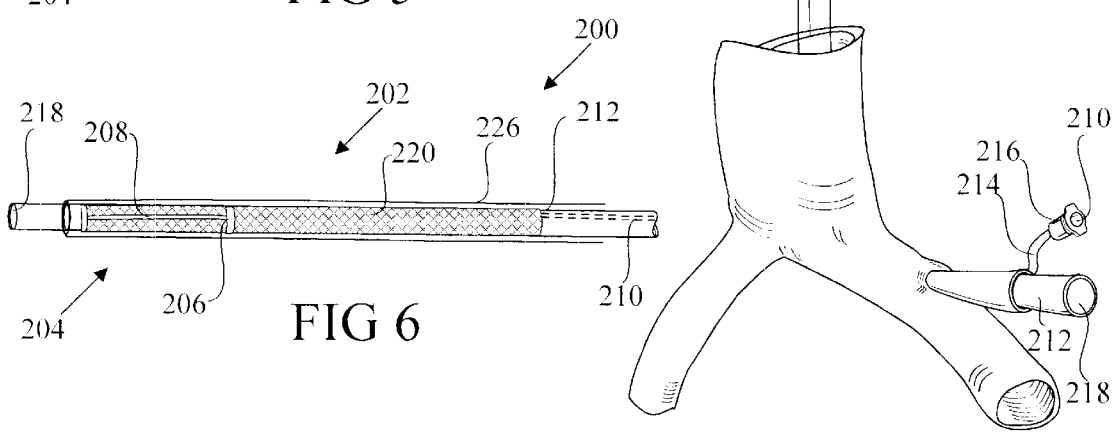

FIGS. 4–6 illustrate a second embodiment of the present invention having an actively deployable CEPA in the form of an embolic filter assembly 202 attached to a perfusion catheter 200. In this embodiment, the filter support structure 204 includes an outer hoop 206 and a plurality of struts 208, which are all interconnected hollow tubular members. Preferably, the outer hoop 206 and the struts 208 are made of a flexible polymeric material. The filter support structure 204 is connected to an inflation lumen 210, which parallels the perfusion lumen 218 within the catheter shaft 212. At its proximal end, the inflation lumen 210 branches off from the catheter shaft 212 to a side arm 214 with a luer fitting 216 for connecting to a syringe or other inflation device. By way of example, this embodiment of the embolic filter assembly 202 is shown with a trumpet-shaped filter screen 220. The filter screen 220 includes a skirt portion 222 extending distally from a proximal, filter pocket 224. The skirt portion 222 is in the shape of a frustum of a cone with an open distal end, which is attached to the outer hoop 206. The filter pocket 224 is roughly cylindrical in shape with a closed proximal end, which is sealingly attached to the catheter shaft 212. The skirt 222 and the filter pocket 224 may be made of the same filter material or they may be made of different filter materials having different porosities. The skirt 222 of the filter screen 220 may even be made of a nonporous material.

The perfusion filter catheter 200 is shown in FIG. 6 with the embolic filter assembly 202 folded into a collapsed position. The outer hoop 206 and the struts 208 of the filter support structure 204 are deflated and the material of the filter screen 220 is folded or collapsed around the catheter shaft 212. An outer tube 226 covers the embolic filter assembly 202 in the collapsed position to facilitate insertion of the catheter 200. Optionally, the outer tube 226 may have a slit or a weakened longitudinal tear line along its length to facilitate removal of the outer tube 226 over the side arm 214 at the proximal end of the catheter 200. Once the perfusion filter catheter 200 is in position within the patient's aorta, the outer tube 226 is pulled back to expose the embolic filter assembly 202. Then, the embolic filter assembly 202 is deployed by inflating the outer hoop 206 and the struts 208 with fluid injected through the inflation lumen 210 to actively expand the filter support structure 204, as shown in FIG. 5. When the embolic filter assembly 202 is deployed, the outer hoop 206 of the filter support structure 204 seals against the inner wall of the aorta, as shown in FIG. 4. Preferably, at least the outer wall of the outer hoop 206 is somewhat compliant when inflated in order to compensate for patient-to-patient variations in aortic luminal diameter.

Figure 7:
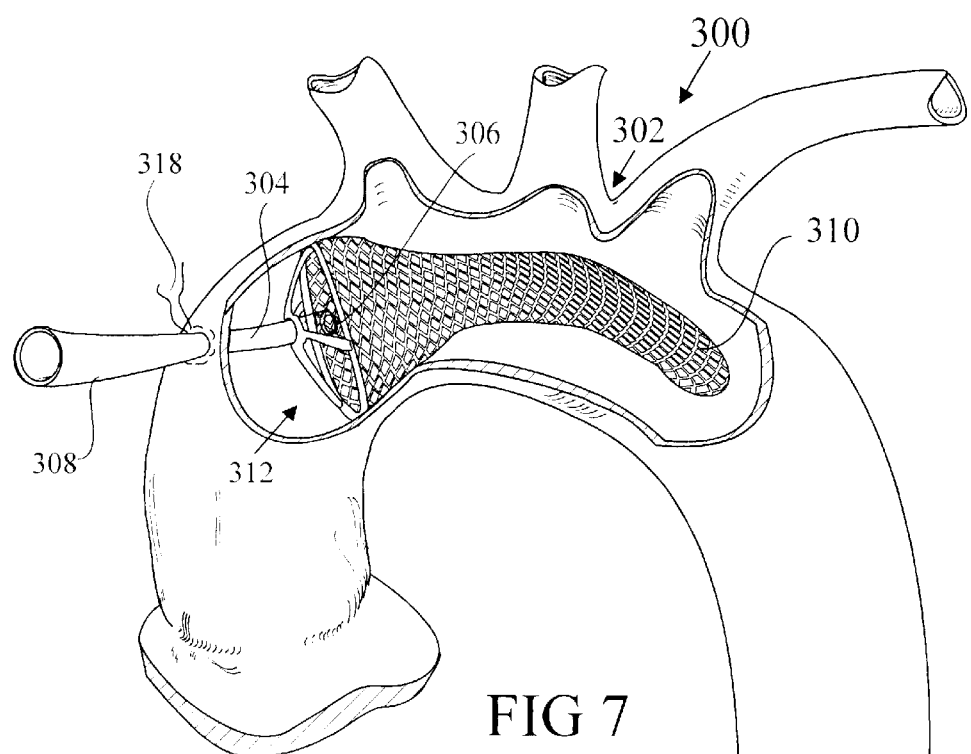
FIGS. 7–9 show a perfusion filter catheter adapted for antegrade deployment via direct aortic puncture.
Figure 8:
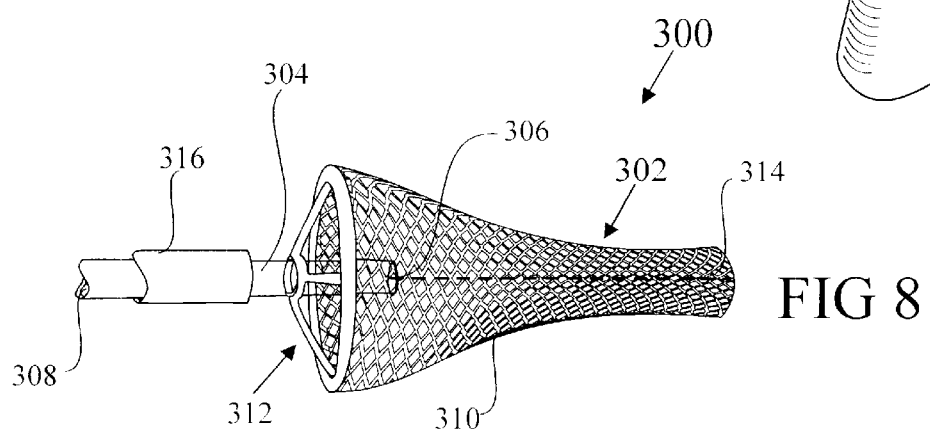
Figure 9:
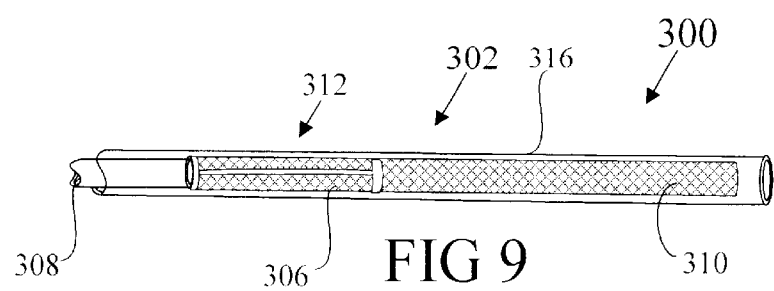

FIGS. 7–9 illustrate a third embodiment of the present invention having a CEPA in the form of a perfusion filter catheter 300 adapted for antegrade deployment via direct aortic puncture. In this exemplary embodiment, the perfusion filter catheter 300 is depicted with a hybrid-style embolic filter assembly 302, which is a compromise between a conical filter screen and a trumpet-style filter. Because the catheter 300 is introduced directly into the ascending aorta, the catheter shaft 304 can be reduced to a length of approximately 20–60 cm and an outside diameter of approximately 12–18 French size (4–6 mm outside diameter) for delivering the 3–4 liters of oxygenated blood needed to preserve organ function during cardiopulmonary bypass. One modification that may be made to the catheter 300 for antegrade deployment is to configure it so that the perfusion port or ports 306 which connect to the perfusion lumen 308 exit the catheter shaft 304 proximal to the filter screen 310 so that fluid flow will come from the upstream side of the embolic filter assembly 302. The catheter shaft 304 need not extend all the way to the distal end of the filter screen 310. The filter screen 310 may be entirely supported by the filter support structure 312, particularly if the embolic filter assembly 302 is to be passively deployed. Alternatively, a small diameter filter support member 314 may extend from the catheter shaft 304 to the distal end of the filter screen 310. If the embolic filter assembly 302 is intended to be actively deployed, the filter support member 314 may be slidably and/or rotatably received within the catheter shaft 304. Either of these configurations allows the embolic filter assembly 302 to be folded or compressed to a size as small as the diameter of the catheter shaft 304 to facilitate insertion of the catheter 300. Optionally, an outer tube 316 may be placed over the folded embolic filter assembly 302 to hold it in the collapsed position.

In use, the ascending aorta of the patient is surgically exposed, using open-chest or minimally invasive surgical techniques. A purse string suture 318 is placed in the ascending aorta and an aortotomy incision is made through the aortic wall. The catheter 300, with the embolic filter assembly 302 in the collapsed position within the outer tube 316, is inserted through the aortotomy and advanced antegrade into the aortic arch. When the proximal end of the embolic filter assembly 302 is positioned in the ascending aorta between the aortic valve and the brachiocephalic artery, the outer tube 316 is withdrawn and the embolic filter assembly 302 is either actively or passively deployed, as shown in FIG. 7. Once the embolic filter assembly 302 is deployed, oxygenated blood may be infused into the aorta through the tubular catheter shaft 304. Any potential emboli are captured by the embolic filter assembly 302 and prevented from entering the neurovasculature or other branches downstream. After use, the embolic filter assembly 302 is returned to the collapsed position, the catheter 300 is withdrawn from the patient, and the purse string suture 318 is tightened to close the aortotomy.

In general, each of the passive and active deployment methods described above may be used interchangeably or together in combinations with each of the embodiments of the perfusion filter catheter and each of catheter insertion methods which are described above and below. Likewise, many of the features of the embodiments described may be used in various combinations with one another to create new embodiments, which are considered to be a part of this disclosure, as it would be too cumbersome to describe all of the numerous possible combinations and subcombinations of the disclosed features. In general, each of the described embodiments may be passively or actively deployed by the methods described above. Each embodiment of the CEPA described can also be adapted for retrograde deployment via peripheral arterial access, such as femoral or subclavian artery access, or for antegrade or retrograde deployment via direct aortic puncture.

Figure 10:
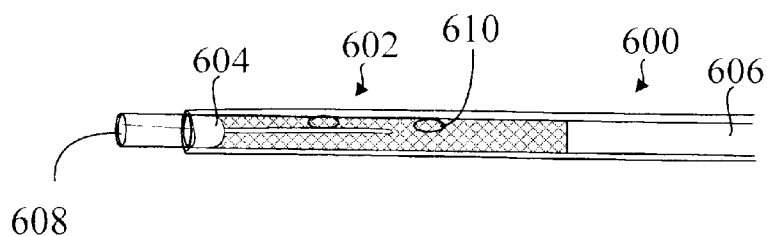
FIGS. 10–14 show the operation of an embodiment of a perfusion filter catheter that combines an embolic filter assembly with a toroidal balloon aortic occlusion device.
Figure 11:
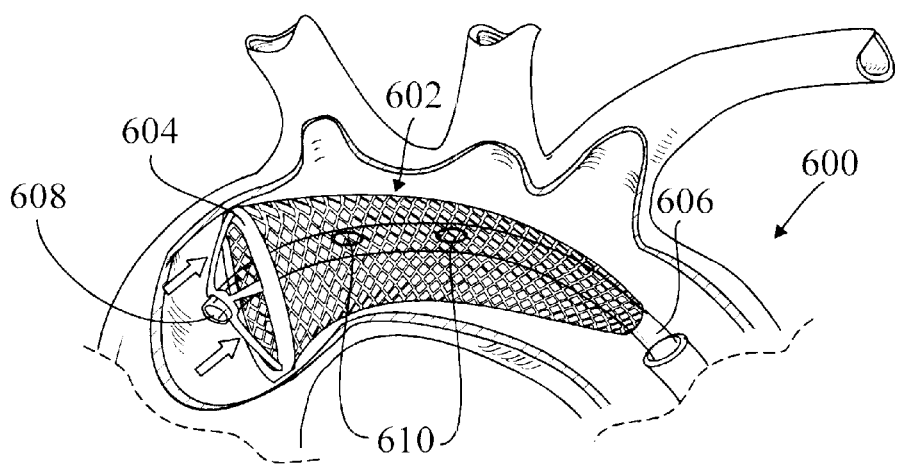
Figure 12:
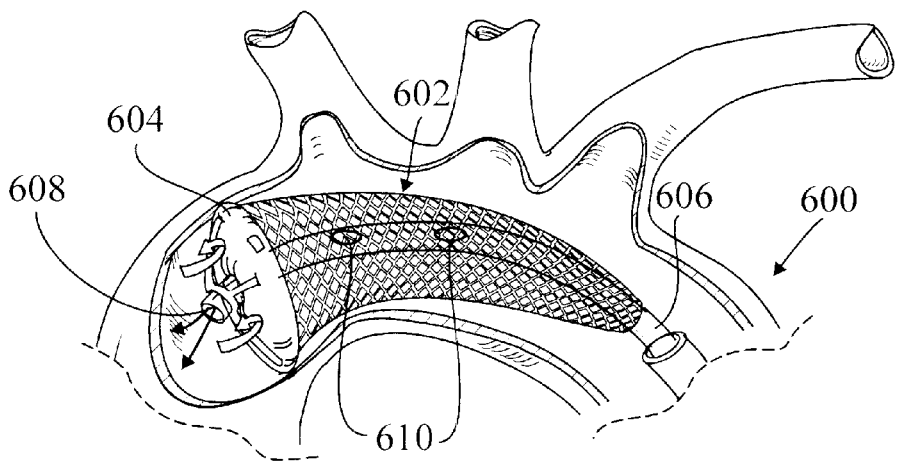

FIGS. 10–12 illustrate a fourth embodiment of the present invention having a CEPA in the form of a perfusion filter catheter 600. FIG. 10 illustrates the CEPA in a collapsed or undeployed state having an embolic filter assembly 602 with a toroidal balloon aortic occlusion device 604 collapsed or folded about the elongated catheter shaft 606. The perfusion filter catheter 600 is inserted in the collapsed state and advanced into the patient's ascending aorta until the embolic filter assembly 602 is positioned between the coronary ostia and the brachiocephalic artery. The toroidal balloon aortic occlusion device 604 is then inflated to expand and deploy the embolic filter assembly 602, as shown in FIG. 11. The embolic filter assembly 602 may assume a simple conical shape or, more preferably, one of the surface area increasing geometries described above. In addition, the embolic filter assembly 602 may include a structure or other means to hold the filter material apart from the aortic wall to maximize the effective filter area. With the embolic filter assembly 602 deployed, cardiopulmonary bypass with embolic protection can be started through the perfusion ports 610.

Figure 13:
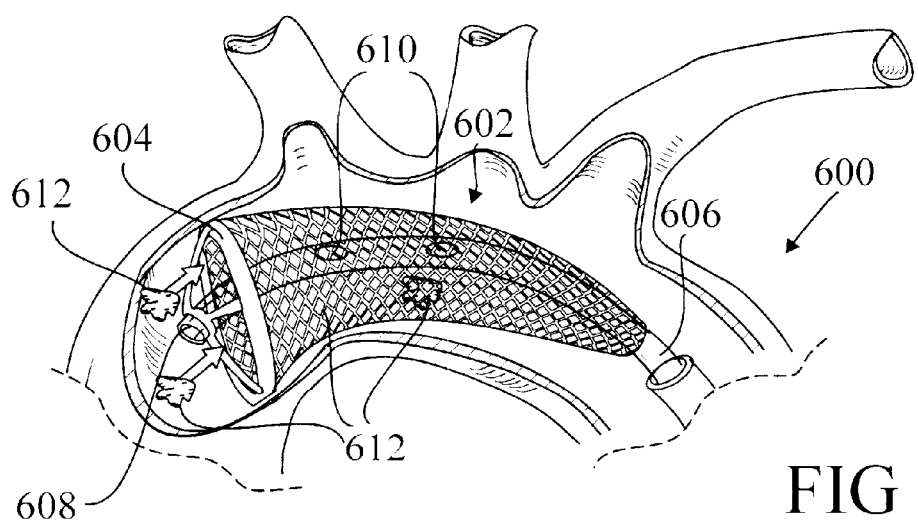
Figure 14:
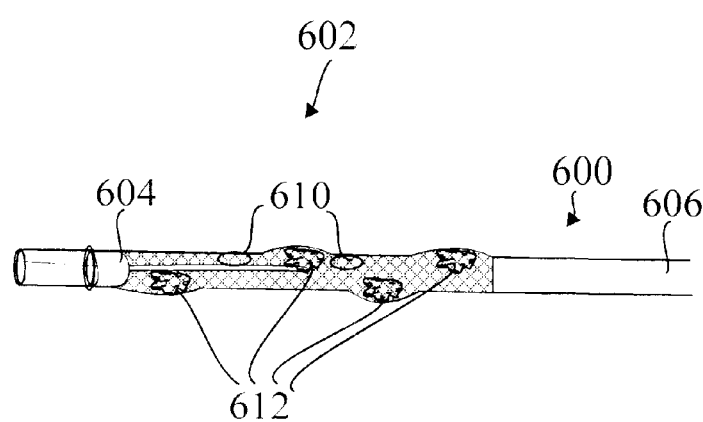

When it is desired to initiate cardioplegic arrest, the toroidal balloon aortic occlusion device 604 is further inflated until it expands inward to occlude the aortic lumen, as shown in FIG. 12. A cardioplegic agent is infused through the cardioplegia port 608 and into the coronary arteries to arrest the heart. Oxygenated blood continues to be infused through the perfusion ports 610. After completion of the surgical procedure, the toroidal balloon aortic occlusion device 604 is partially deflated, leaving the embolic filter assembly 602 deployed, as shown in FIG. 13. Oxygenated blood enters the coronary arteries to restart the heart beating. If any embolic materials 612 are dislodged during manipulation of the heart or when the heart resumes beating, they will be captured by the embolic filter assembly 602. Once the patient is weaned off bypass, the toroidal balloon aortic occlusion device 604 is deflated to collapse the embolic filter assembly 602, as shown in FIG. 14. Any potential emboli are trapped within the embolic filter assembly 602 and can be removed along with the catheter 600.

Figure 15:
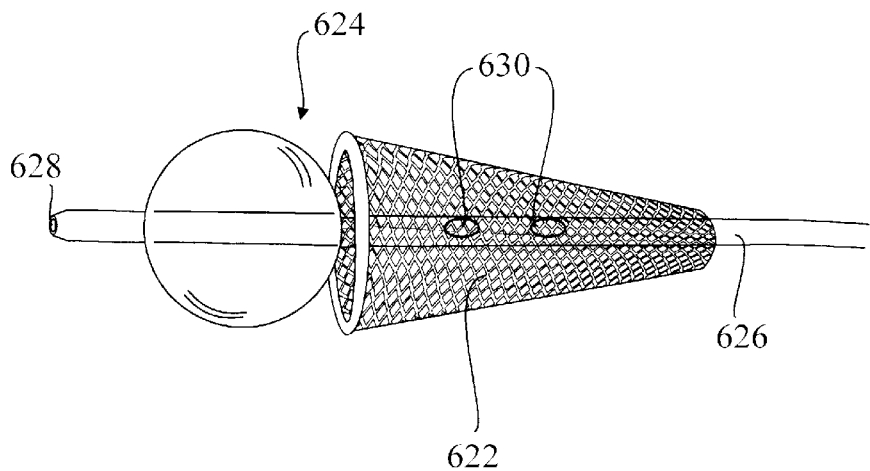
FIG. 15 shows an embodiment of a perfusion filter catheter that combines an embolic filter assembly with an inflatable balloon aortic occlusion device.

FIG. 15 illustrates a fifth embodiment of the present invention having a CEPA in the form of an embolic filter assembly 622 with an inflatable balloon aortic occlusion device 624. The embolic filter assembly 622 may be any one of the actively or passively deployed embolic filter assemblies described herein. Preferably, the inflatable balloon aortic occlusion device 624 is an elastomeric balloon of sufficient inflated diameter to occlude the ascending aorta and is mounted on the elongated catheter shaft 626 upstream of the embolic filter assembly 622. Alternatively, the inflatable balloon aortic occlusion device 624 may be positioned to occlude the inlet end of the embolic filter assembly 622 to minimize the area of contact between the perfusion filter catheter 620 and the aortic wall. The inflatable balloon aortic occlusion device 624 is connected to an inflation lumen within the elongated catheter shaft 626. A cardioplegia lumen, which may also serve as a guidewire lumen, connects to a cardioplegia port 628 at the distal end of the catheter shaft 626. A perfusion lumen connects to one or more perfusion ports 630 located on the catheter shaft 626 downstream from the inflatable balloon aortic occlusion device 624, but upstream of the embolic filter assembly 622. The operation of the perfusion filter catheter 620 of FIG. 15 is quite similar to that described for the embodiment of FIGS. 10–14.

Figure 16:
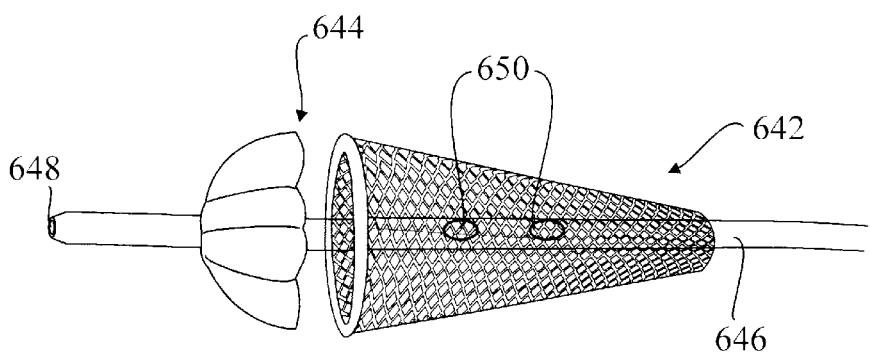
FIG. 16 shows an embodiment of a perfusion filter catheter that combines an embolic filter assembly with a selectively deployable external catheter flow control valve.

FIG. 16 illustrates a sixth embodiment of the present invention having a CEPA in the form of an embolic filter assembly 642 combined with a selectively deployable external catheter flow control valve 644. The embolic filter assembly 642 may be any one of the actively or passively deployed embolic filter assemblies described herein. The selectively deployable external catheter flow control valve 644 is mounted on the elongated catheter shaft 646 upstream of the embolic filter assembly 642. Alternatively, the selectively deployable external catheter flow control valve 644 may be positioned to occlude the inlet end of the embolic filter assembly 642 to minimize the area of contact between the perfusion filter catheter 640 and the aortic wall. Selectively deployable external catheter flow control valves suitable for this application are described in commonly owned, copending U.S. patent applications Ser. Nos. 08/665,635, 08/664,361 and 08/664,360, filed Jun. 17, 1996, which are hereby incorporated by reference in their entirety. The elongated catheter shaft 646 may include one or more deployment lumens as needed for actuating the external catheter flow control valve 644. A cardioplegia lumen, which may also serve as a guidewire lumen, connects to a cardioplegia port 648 at the distal end of the catheter shaft 646. A perfusion lumen connects to one or more perfusion ports 650 located on the catheter shaft 646 downstream from the external catheter flow control valve 644, but upstream of the embolic filter assembly 622. The operation of the perfusion filter catheter 640 of FIG. 16 is quite similar to that described for the embodiment of FIGS. 10–14.

Figure 17:
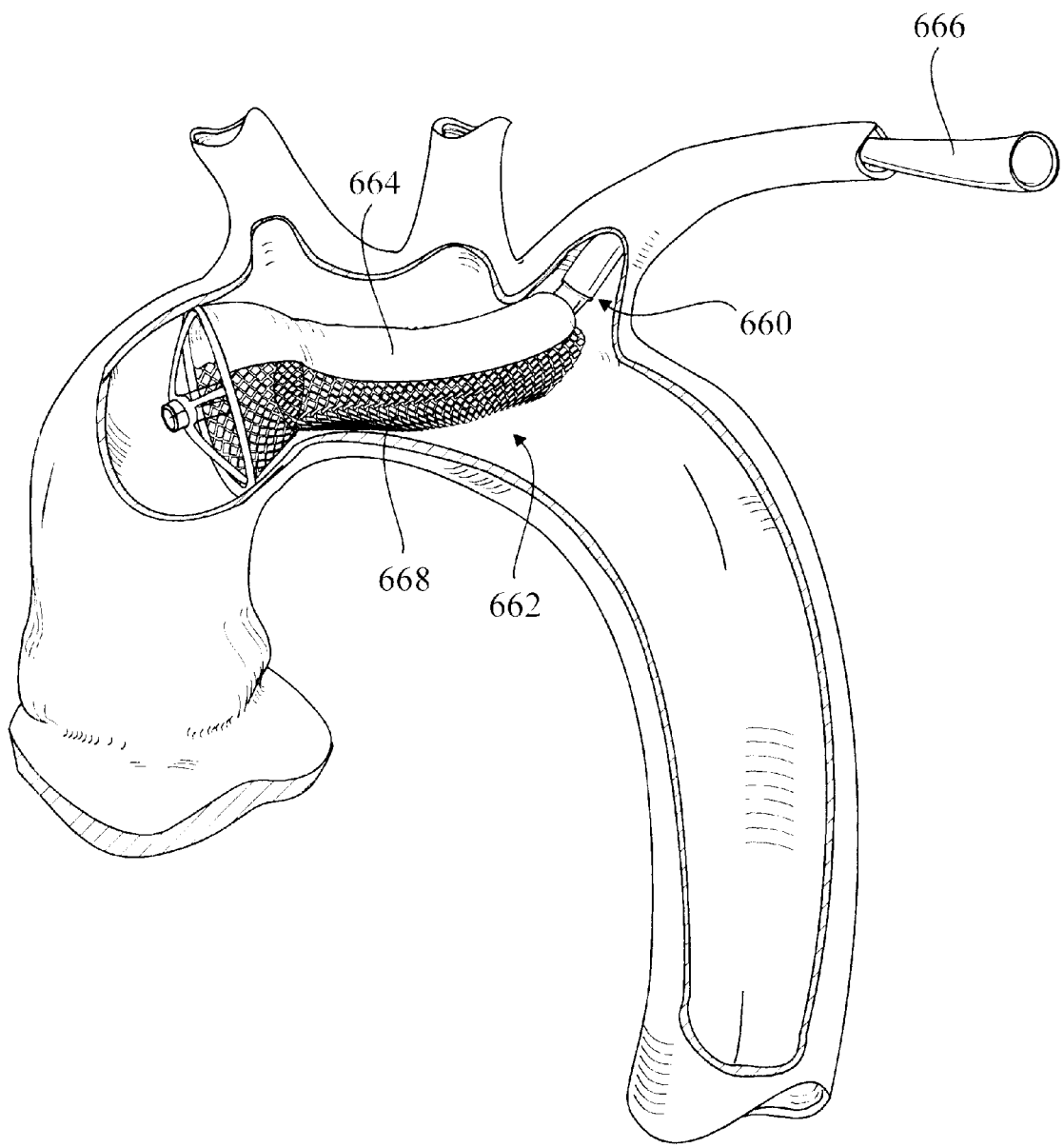
FIG. 17 shows an embodiment of a perfusion filter catheter with an embolic filter assembly having areas of different filter porosity.

FIG. 17 illustrates a seventh embodiment of the present invention having a CEPA capable of being used in combination with many of the features and embodiments previously described. FIG. 17 shows an embodiment of a perfusion filter catheter 660 with a CEPA in the form of an embolic filter assembly 662 having areas of different filter porosity. The embolic filter assembly 662 is mounted on an elongated catheter shaft 666 that can be adapted for peripheral introduction via the femoral artery or subclavian artery or for central insertion directly into the ascending aorta either through a median sternotomy, transternally, thoracotomy or an intercostal space. The embolic filter assembly 662 may resemble any one of the actively or passively deployed embolic filter assemblies described herein. Preferably, the embolic filter assembly 662 assumes one of the surface area increasing geometries described above, such as a trumpet-style embolic filter assembly 662 as shown. The embolic filter assembly 662 is divided along a longitudinal dividing line into areas of different filter porosity. In a preferred embodiment, the embolic filter assembly 662 has an upper portion 664 of finer porosity facing toward the aortic arch vessels and a lower portion 668 of courser porosity facing away from the aortic arch vessels. Preferably, the elongated catheter shaft 666 will have a preformed curve to help orient the upper portion 664 and the lower portion 668 of the embolic filter assembly 662 in the proper position once deployed. The filter mesh of the upper portion 664 may be selected to exclude both macroemboli and microemboli, and the filter mesh of the lower portion 668 may be selected to exclude macroemboli only. Alternatively, the upper portion 664 may be impermeable so as to act like a shunt to direct potential emboli downstream away from the aortic arch vessels.

Another feature that may be combined with the features and embodiments of the present invention is an aortic transillumination system or infrared emitting means for locating and monitoring the position of the catheter, the filter and the optional occlusion devices without fluoroscopy by transillumination of the aortic wall. Aortic transillumination systems using optical fibers and/or light emitting diodes or lasers suitable for this application are described in commonly owned, copending U.S. patent application Ser. No. 60/088,652, filed Jun. 9, 1998 and its corresponding utility application Ser. No. 09/326,816 filed Jun. 7, 1999, which are hereby incorporated by reference in their entirety.

FIGS. 18–21 illustrate an eighth embodiment of the present invention having a CEPA in the form of an aortic flow divider. The flow divider 810 may be formed in a variety of configurations, however the flow divider 810 in the undeployed state will be contained in a relatively small volume around the circumference of the distal end of the catheter and in the deployed state will have a length and width sufficient to divide blood flow in the aorta in the vicinity of the ostia of the arch vessels. In the undeployed state, the flow divider 810 is collapsible around the catheter shaft creating a low profile not significantly larger than the outer diameter of the catheter body. The flow divider 810 may comprise one or more inflatable chambers, the chambers all being in fluid communication, or one or more selectively deployable shrouds. The inflatable chambers may be relatively non-compliant or they may be compliant, exhibiting elastic behavior after initial inflation, for example, to closely fit the size, shape and curvature of the aortic lumen.

The catheter may further include one or more additional or auxiliary flow control members located on the catheter either distal or proximal from the flow divider 810 to further segment the patient's circulatory system for selective perfusion to different organ systems within the body or to assist in anchoring the catheter in a desired position. These auxiliary flow control members may comprise inflatable balloons or selectively deployable external catheter valves as described in connection with to FIGS. 15 and 16. Preferably, the flow divider 810, and any auxiliary flow control members, or anchoring members, if present, are mounted directly on an elongated catheter shaft. In a preferred embodiment, the catheter shaft includes at least three lumens, one lumen for inflating or otherwise deploying the flow divider 810, a second for perfusion of the arch vessels, and a third guidewire lumen. In alternate embodiments, additional lumens may be included for deploying the auxiliary flow control members, for measuring the pressure at desired locations within the aorta, or for perfusing other isolated segments of the patient's circulatory system. Suitable methods and apparatus for performing isolated segmental perfusion for use in conjunction with the present invention are described in commonly owned, copending U.S. patent application Ser. No. 60/084,835 filed May 9, 1998 and its corresponding utility application Ser. No. 09/306,555 filed May 6, 1999, which are hereby incorporated by reference in their entirety.

The catheter may be configured for retrograde deployment via a peripheral artery, such as the femoral artery, or it may be configured for antegrade deployment via an aortotomy incision or direct puncture in the ascending aorta. The catheter is characterized by a flexible catheter shaft placed by surgical cutdown or Seldinger technique into the vessels of the lower or upper extremity or neck. Other large internal vessels may also be used.

Anticoagulants, such as heparin and heparinoids, may be applied to the surfaces of the catheter and/or flow control members as desired. Anticoagulants may be painted or sprayed onto the device. Anticoagulants other than heparinoids may also be used, for example monoclonal antibodies such as REOPRO (Eli Lilly and Co., Indianapolis, Ind.). A chemical dip comprising the anticoagulant may also be used. In addition an echogenic coating may also be applied to the catheter to enhance visualization. Other methods known in the art for applying chemicals to catheters may be used.

Figure 18:
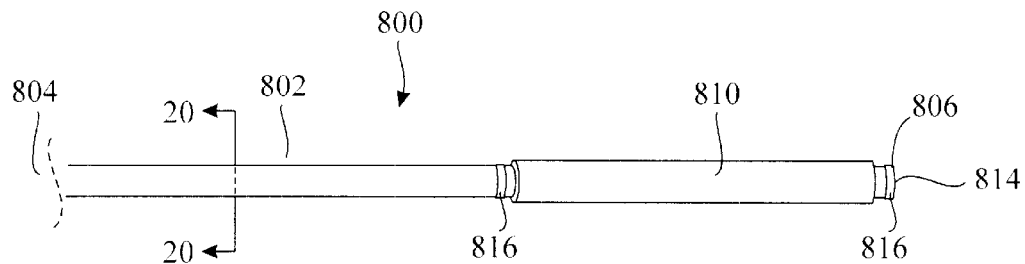
FIG. 18 shows a bottom view of another CEPA of the present invention configured for retrograde deployment via a peripheral artery access point, such as the femoral artery.

FIG. 18 illustrates the aortic catheter 800 of the present invention having an elongated catheter shaft 802 with a proximal end and a distal end. The proximal end 804 preferably extends out of the patient's body and the distal end 806 is closest to the patient's heart. The elongated catheter shaft 802 preferably has an overall length sufficient to reach from the arterial access point to a selected location within a patient's aorta. For femoral artery deployment in adult human patients, the elongated catheter shaft 802 preferably has an overall length from approximately 60 cm to 120 cm, and more preferably 70 cm to 90 cm.

In one illustrative embodiment, the elongated catheter shaft 802 has an outer diameter that is preferably approximately 9 to 22 French (3.0 to 7.3 mm), and more preferably 12 to 18 French (4.0 to 6.0 mm) for use in adult human patients. Catheters for pediatric use, or use in non-human subjects, may require different dimensions and would be scaled accordingly. The elongated catheter shaft 802 is preferably formed of a flexible thermoplastic material, a thermoplastic elastomer, or a thermoset elastomer. Suitable materials for use in the elongated catheter shaft 802 include, but are not limited to, polyvinylchloride, polyurethane, polyethylene, polyamides, polyesters, silicone, latex, and alloys or copolymers thereof, as well as braided, coiled or counterwound wire or filament reinforced composites. Additionally or alternatively, the elongated catheter shaft 802 may be constructed using metallic tubing or a solid wire, for example stainless steel hypodermic tubing or wire or superelastic nickel-titanium alloy tubing or wire. Preferably, the aortic catheter 800 includes one or more location markers 816, such as radiopaque markers and/or sonoreflective markers, to enhance imaging of the aortic catheter 800 during deployment using standard fluoroscopy, ultrasound, MRI, MRA, transesophageal echocardiography, or other techniques. For example, in the illustrative embodiment shown in FIG. 18, a radiopaque location marker 816 is positioned near the distal end 806 of the catheter shaft 802, and another near the proximal end of the flow divider 810, to assist in positioning the flow divider 810 within the aortic arch. The radiopaque location markers 816 may be formed as a ring or disk of dense radiopaque metal such as gold, platinum, tantalum, tungsten, or compounds or alloys thereof, or a ring of a polymer or adhesive material heavily loaded with a radiopaque filler material.

The flow divider 810, of FIG. 18, is mounted proximate the distal end 806 of the elongated catheter shaft 802. The embodiment shown in FIGS. 18 through 21, shows the flow divider 810 in the form of a flat elongate expandable inflatable balloon or mattress bonded to the catheter shaft 802 by heat welding or with an adhesive. The inflatable flow divider 810 has a deflated state in which the flow divider 810 adheres closely to the catheter shaft 802 so that the collapsed diameter of the flow divider 810 is, preferably, not substantially larger than the diameter of the catheter shaft 802, and an inflated state in which the flow divider 810 expands to dimensions sufficient to divide blood flow in the aortic arch of the patient into two fluid flow channels. The distal end of the flow divider may expand beyond the distal end of the catheter as illustrated in FIG. 21 or alternatively may expand to a distance equal to or less than the distal end. Preferably, the flow divider 810 will be formed so that, when inflated, the flow divider 810 automatically assumes and maintains a desired shape, without any additional stiffening structure. However, in some embodiments, it may be desirable to include means for assisting the flow divider 810 in maintaining a desired shape, and any known means for accomplishing this may be used. For example, the divider may include ribs or other stiffening structures coupled to the flow divider 810, or formed as an integral part of the flow divider 810. Alternatively, the flow divider 810 may include mattress type welds, or internal welds or columns. The outer surface of flow divider 810 may include a friction increasing means such as a friction increasing coating or texture to increase friction between the flow divider 810 and the aortic wall, to assist in maintaining the flow divider 810 in a desired position within the aorta, when deployed.

Figure 19:
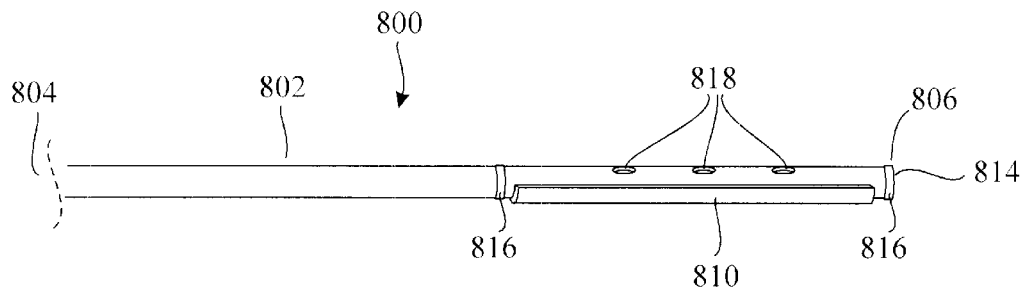
FIG. 19 shows a side view of the catheter of FIG. 18, showing the CEPA in the form of a divider in the collapsed state.

FIG. 19 is a side view of the catheter 800, showing that the flow divider 810 is preferably coupled only to a portion of the diameter of the catheter shaft 802. Thus, perfusion ports 818 are unobstructed. Alternatively, the flow divider may be mounted above the perfusion ports 818 wherein the material covering the ports 818 is skived or cut away to allow for perfusion therethrough. In the inflatable embodiments a heat seal can be created around the skived out area or in the case of mattress type welds the skived area can be in an area of an already existing weld. Furthermore, the material covering the ports 818 may only be partially cut away leaving part of the port covered in order to help facilitate the direction and flow of fluid out the ports 818. In addition, FIG. 21 illustrates the catheter shaft 802 being substantially centered relative to the divider 810, alternative embodiments can have the catheter shaft off center, tangential or in any geometric position that helps facilitate placement and optimal flow.

Figure 20:
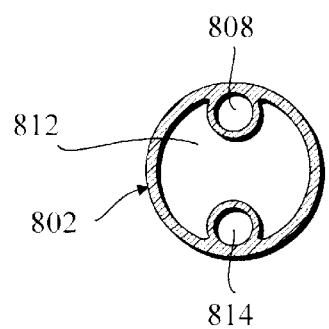
FIG. 20 shows a cross section of the aortic catheter of FIG. 18 taken along line 20—20 in FIG. 18.
Figure 21:
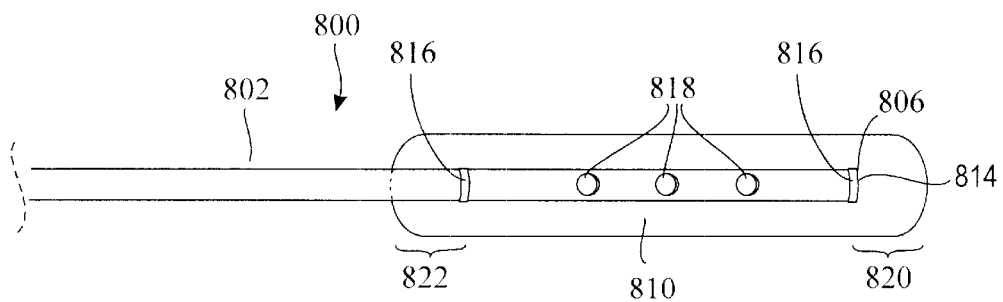
FIG. 21 shows a top view of the catheter of FIG. 18 with the flow divider deployed.

FIG. 20 is a cross section of the catheter shaft 802 taken along line 20—20 of FIG. 18. The elongated catheter shaft 802 preferably has at least three lumens, an inflation lumen 808 that is used to deploy the flow divider 810, a perfusion lumen 812 that is used to perfuse one or both of the fluid flow channels, and a guidewire lumen 814. The configuration of the lumens is shown for illustrative purposes only, and any reasonable configuration of lumens within the catheter may be used. Furthermore, additional perfusion lumens may be added to perfuse both of the fluid flow channels separately and independently. Additional fluid ports similar to ports 818 only positioned in the other fluid flow channel would also be necessary.

The flow divider 810 is shown in a deployed state in FIG. 21. Preferably, the flow divider 810 in its deployed configuration includes a distal portion 820 that extends beyond the distal end of the catheter 800 in order to seal or touch against the aortic lumen wall. The proximal portion 822 of the divider 810 is shown shaped similarly to the distal portion 820, however, in this embodiment the shape of the proximal portion 822 of the divider 810 is not critical to the invention and could be triangular, square, or any other desired shape. In other embodiments, it may be preferable that the shape be chosen to encourage low turbulence, or possibly laminar, fluid flow where the fluid flow from the flow channel above the divider 810 and the fluid flow from below the flow divider 810 meet at the trailing edge of the proximal portion 822. However in a preferred embodiment, the divider is constructed such that any flow around the catheter is directed toward the corporeal circulation and not to the arteries leading to the brain. One preferred method for accomplishing such desirable flow characteristics is to direct any excess flow to the arch around the proximal portion 822 of the divider and down to the corporeal circulation. Such a flow relationship protects the brain by directing any extra flow into the second fluid path and away from the brain. This is also beneficial in that no real seal is necessary, but rather laminar flow is established and emboli are directed away from the divider and the brain by the fluid flow. Even if turbulence results near the trailing edge of the flow divider 810, embolic material in the blood will have already passed the arch vessels, thereby achieving the objective of preventing embolic material from entering the cerebral circulatory system.

It may not be essential that the edges of the flow divider 810 create a perfect seal or any seal with the wall of the aorta. Some leakage of blood around the flow divider 810 may be tolerated because the fluid perfused through the perfusion lumen 812 creates a pressure gradient from above the flow divider 810 to below the flow divider 810 so that any potential embolic material will not enter the flow channel above the flow divider 810.

Figure 22:
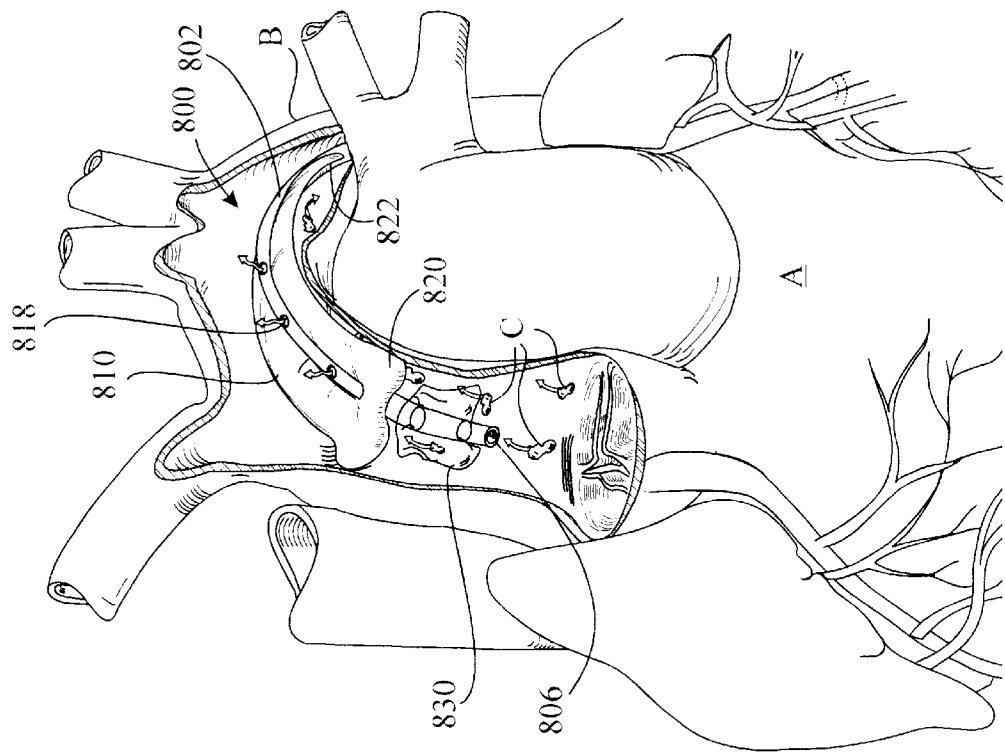
FIG. 22 shows a perspective view of an embodiment of the catheter of the invention including a deployed auxiliary flow control member positioned between the flow divider and the distal end of the catheter.
Figure 23:
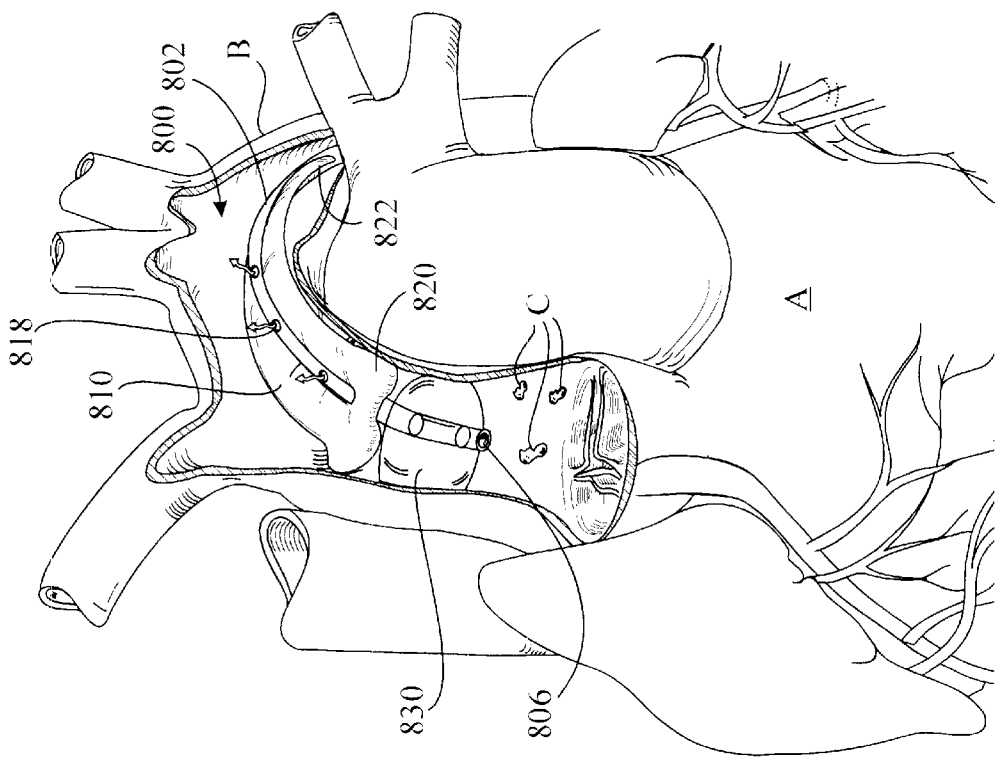
FIG. 23 shows a perspective view of the catheter of FIG. 22 with the auxiliary flow control member partially collapsed.

Any embodiments of the catheter 800 of the invention described above may further include auxiliary flow control members. The auxiliary flow control members may be used to further compartmentalize the patient's circulatory system, or may be used for other functions such as assisting in securely anchoring the catheter in a chosen position. An example of a catheter of the invention further comprising an auxiliary flow control member is seen in FIGS. 22 and 23, which illustrate an auxiliary flow control member 830 coupled to the distal end of the catheter 800 proximate the distal end 122 of the flow divider 810. The auxiliary flow control member 830 is positioned within the aorta and can be fully deployed to occlude or substantially occlude the aorta. The auxiliary flow control member 830 shown in FIG. 22 is an inflatable balloon bonded to the catheter shaft 802 by heat welding or with an adhesive. Alternatively, the auxiliary flow control member 830 could be a deployable valve, or other structure. Deployable valves suitable for use in this application are described in commonly owned U.S. Pat. Nos. 5,827,237 and 5,833,671, which have been previously incorporated by reference. Suitable materials for the inflatable balloon include, but are not limited to, elastomers, thermoplastic elastomers, polyvinylchloride, polyurethane, polyethylene, polyamides, polyesters, silicone, latex, and alloys or copolymers and reinforced composites thereof. In alternate embodiments, the auxiliary flow control member 830 may be positioned on the proximal side of the flow divider 810, if desired. The auxiliary flow control member 830 may also be used to anchor the catheter 800 so that it does not migrate out of its optimal position during the medical procedure. The outer surface of an auxiliary flow control member 830 used to anchor the catheter 800 may include a friction increasing means, such as a friction increasing coating or texture, to increase friction between the auxiliary flow control member 830 and the aortic wall, when deployed. Alternatively, an auxiliary flow control member 830, which may be an inflatable balloon or deployable valve, can be mounted on a separate catheter and introduced through a lumen within the catheter 800.

FIGS. 22 and 23 show the flow divider 810 fully deployed, and the auxiliary flow control member 830 partially collapsed and fully deployed. As blood flow resumes from the heart A, embolic material C is diverted away from the arch vessels by the flow divider 810.

Figure 24:
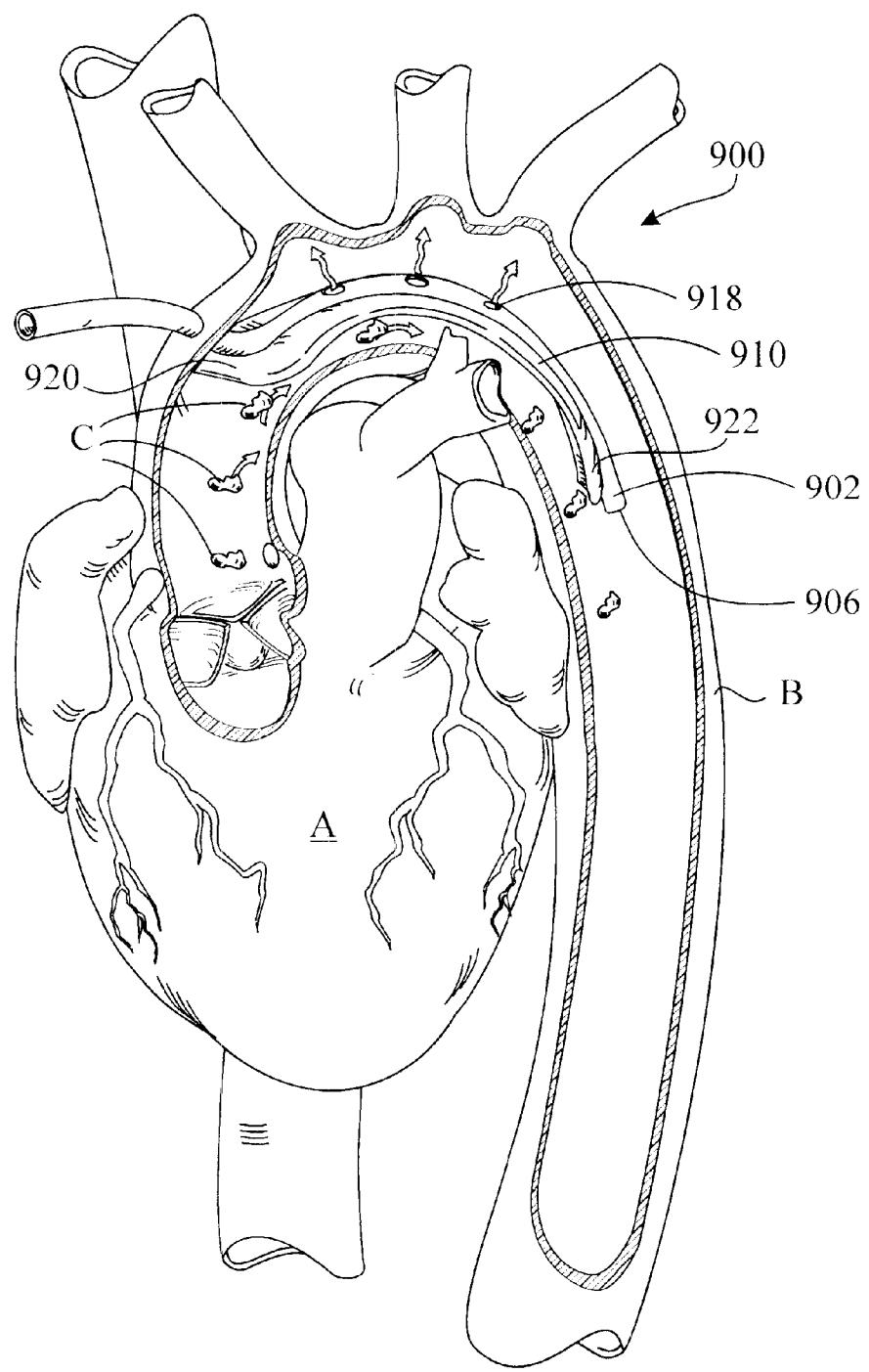
FIG. 24 shows an embodiment of the catheter of the invention configured for antegrade deployment.

The previous embodiments have been described using a catheter configured for a retrograde approach to the aorta from a peripheral vessel such as the femoral artery. The invention could easily be modified for alternate deployment means. For example, FIG. 24 shows a catheter 900 configured for central antegrade deployment in the aortic arch through an aortotomy or direct puncture in the ascending aorta. The catheter 900 and flow divider 910 are configured similarly to the catheters disclosed in previous embodiments. Other embodiments of the invention may be configured for peripheral insertion through the subclavian or axillary arteries.

Figure 25:
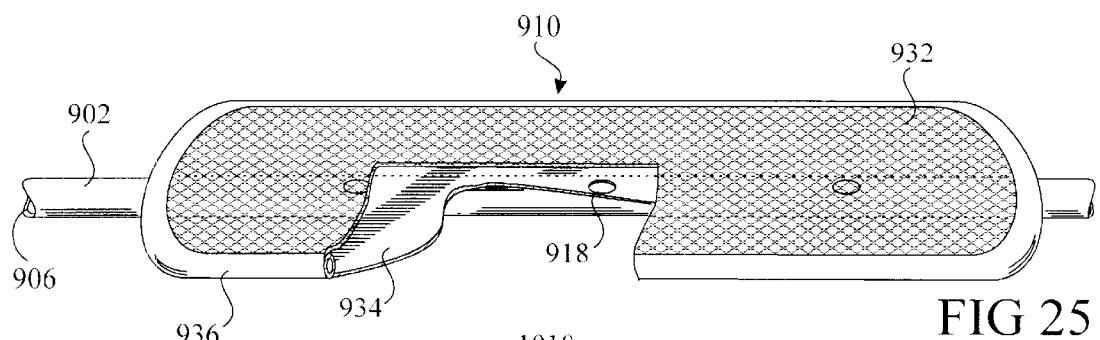
FIG. 25 shows a cut-away view of an embodiment of the flow divider including a mesh or porous portion for perfusing from the upper surface of the flow divider.

FIG. 25 discloses an alternate embodiment of the flow divider 910, wherein the top surface of the flow divider 910 comprises a mesh or porous region 932. The perfusion ports 918 allow a selected fluid to enter the interior chamber 934 of the flow divider 910 before the fluid passes through the mesh or porous region 932 to perfuse the aorta. The material or materials used in the flow divider 910 are preferably characterized by properties that allow an internal pressure within the flow divider 910 to be maintained at a sufficient level to maintain the deployed configuration of the flow divider 910 to divide the aorta, while also allowing a controlled volume of fluid to escape from the flow divider 910 through the mesh or porous region 932 on the upper surface of the flow divider 910 for perfusing the arch vessels. Thus, the surface of the flow divider 910 may have porous regions that allow a fluid to be perfused at a known rate when a specific pressure is attained. The inflatable peripheral tube 936 surrounds the periphery of the flow divider 910, however, in alternate embodiments, this feature may be omitted. In embodiments including an inflatable peripheral tube 936, it is preferable that the peripheral tube 936 be inflated from a separate additional lumen.

Figure 26:
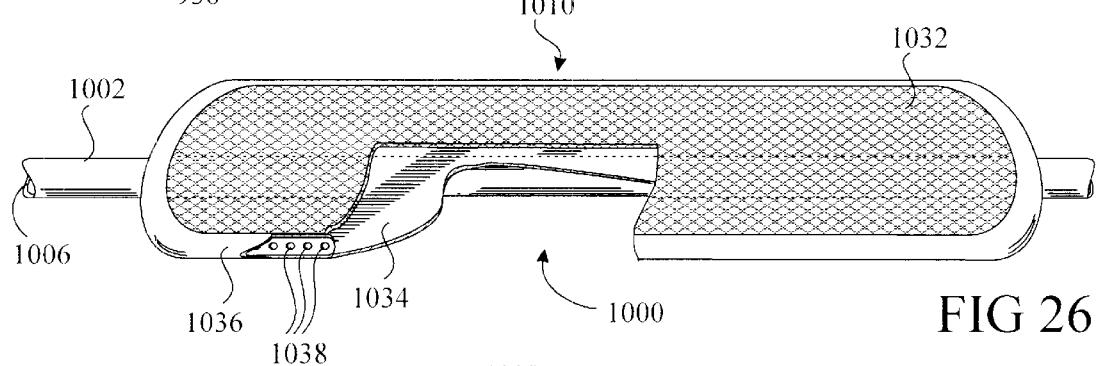
FIG. 26 shows a cut-away view of an alternate internal structure of the flow divider of FIG. 25.

FIG. 26 discloses an embodiment of the flow divider 910 of FIG. 25 wherein a single inflation and perfusion lumen may be used. In this embodiment, perfused fluid passes through a lumen 1006 in the shaft 1002 of the catheter 1000 into the peripheral tube 1036 to inflate the peripheral tube 1036. Apertures 1038 between the inflatable peripheral tube 1036 and the interior chamber 1034 of the flow divider 1010 allow fluid to flow from the peripheral tube 1036 into the chamber 1034 within the inflatable flow divider 1010. The fluid then passes through the mesh or porous region 1032 of the flow divider 1010 to perfuse the aorta. Preferably, the apertures 1038 of the peripheral tube 1036 are sized so that the pressure within the peripheral tube 1036 is higher than the pressure within the chamber 1034 of the flow divider 1010.

The porous and non-porous sections of the flow divider 1010 may be formed from the same or separate materials. Suitable materials for the non-porous portions of the flow divider 1010 include, but are not limited to, elastomers, thermoplastic elastomers, polyvinylchloride, polyurethane, polyethylene, polyamides, polyesters, silicone, latex, and alloys or copolymers, and reinforced composites thereof. Suitable materials for the porous portions of the flow divider 1010 include meshes, woven and nonwoven fabrics, and porous membranes, such as microperforated or laser perforated polymer or elastomer films. For example, polyester meshes may be used, such as meshes made by Saati Corporation and Tetko, Inc. These are available in sheet form and can be easily cut and formed into a desired shape. Other meshes and porous materials known in the art, which have the desired characteristics, are also suitable.

Figure 27:
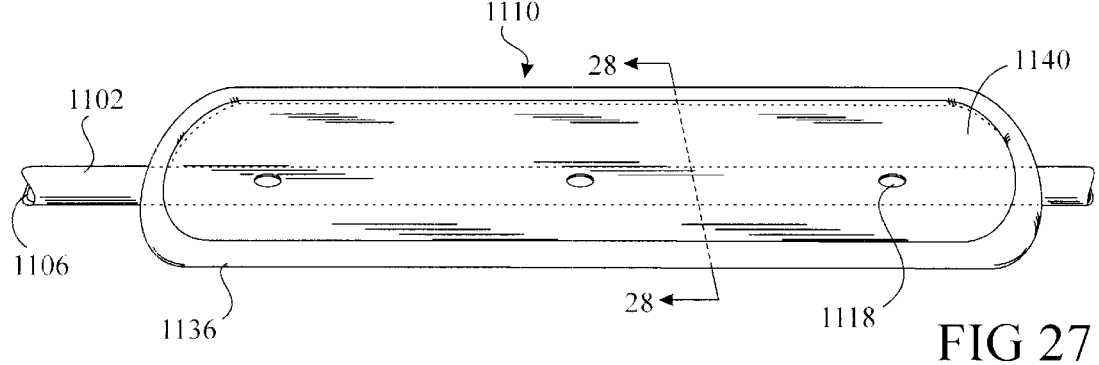
FIG. 27 shows an embodiment of the flow divider of the invention comprising a peripheral tube and membrane structure.
Figure 28:
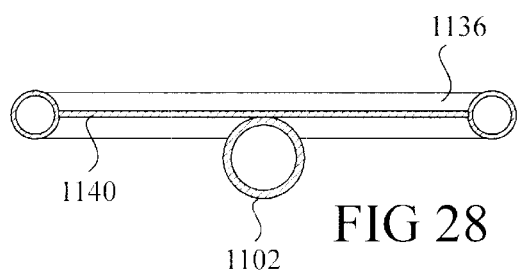
FIG. 28 shows a cross section of the flow divider of FIG. 27 taken along line 28—28.

Referring to FIG. 27, an embodiment of the flow divider 1110 is disclosed having a nonporous film 1140 surrounded by a peripheral tube 1136 acting as a support structure. Inflation of the peripheral tube 1136 causes deployment of the film 1140 within the aorta. Holes are positioned over the perfusion apertures 1118 to allow perfusion of the region above the flow divider 1110. FIG. 28 is a cross section view of the flow divider 1110 of FIG. 27 taken along line 28—28. It is possible to make the flow divider 1110 of FIG. 27 by fabricating an oval balloon and affixing the central portion of the top and bottom layers together, leaving a peripheral region where the upper and lower layers are not coupled together, forming the inflatable peripheral tube 1136. Alternatively, the peripheral tube 1136 and film 1140 of the flow divider 1110 may be formed of separate components and affixed together by a known means for joining such materials, such as by heat welding or adhesives.

Figure 29:
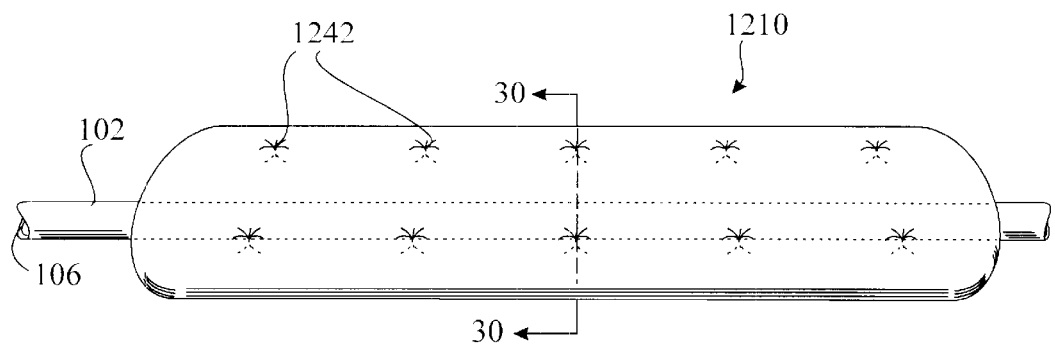
FIG. 29 shows an embodiment of the flow divider of the invention with welds or joined areas between an upper and a lower film of the flow divider to give additional structure and rigidity to the flow divider.
Figure 30:
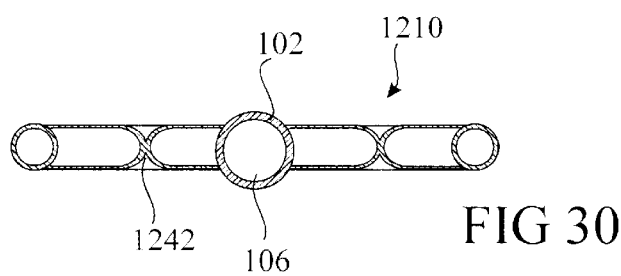
FIG. 30 shows a cross section of the flow divider of FIG. 29 taken along line 30—30 of FIG. 29.
Figure 31:
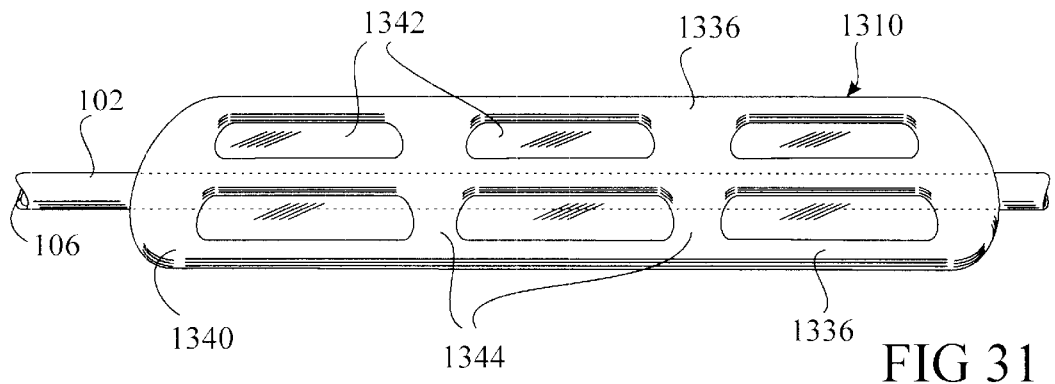
FIG. 31 shows an alternate embodiment of FIG. 29 with larger joined areas between the upper and lower films of the flow divider.

FIGS. 29–31 represent alternate embodiments of the flow divider 1210 with welds or joined areas between an upper and a lower film of the flow divider 1210 to give additional structure and rigidity to the flow divider 1210. FIG. 29 discloses an embodiment wherein the interior surface of the upper film has been coupled 1242 to the interior surface of the lower film, preferably by spot heat welding or adhesive. The resulting structure maintains the geometry of the flow divider 1210 and provides it with additional rigidity. FIG. 30 is a cross section view of the flow divider 1210 of FIG. 29 taken along line 30—30 of FIG. 29. FIG. 31 shows an alternate embodiment of FIG. 29 with larger joined areas 1342 between the upper and lower films of the flow divider 1310, creating a well defined peripheral tube 1336 and lateral or branch support members 1344. In alternative embodiments, the film 1340 and peripheral tube 1336 and lateral or branch support members 1344 maybe fabricated as separate components and joined using any known means for doing so, including the use of adhesive or heat welding.

Figures 32, 33:
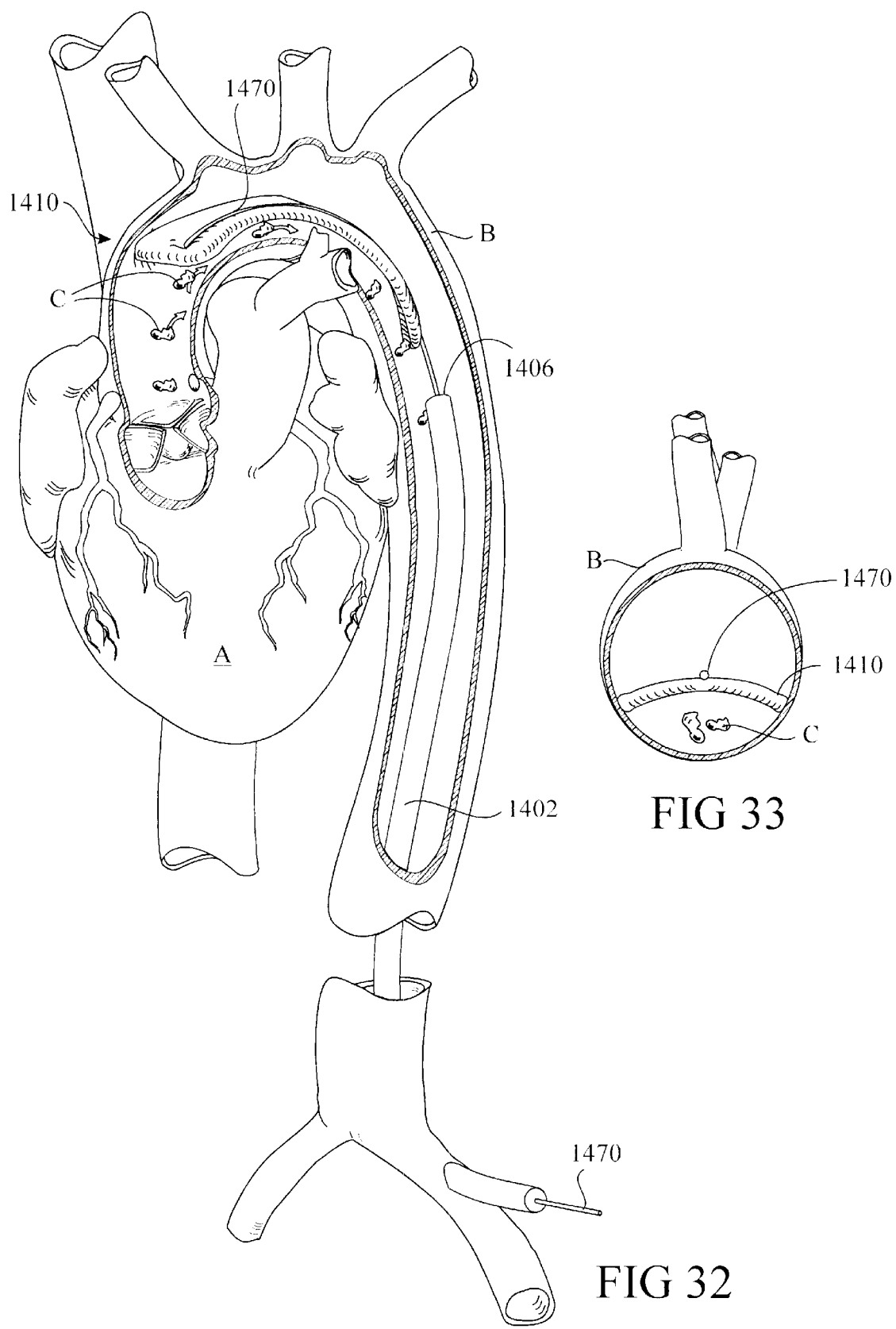
FIG. 32 shows another embodiment of the flow divider of the invention deployed from a lumen within a catheter.
FIG. 33 shows a cross section of the flow divider and aorta of FIG. 32 taken transversely through the aorta.

All of the previously described flow divider embodiments have been deployed from the external surface of the catheter shaft. However, in other embodiments, the flow divider may be deployed from within one or more lumens in the catheter shaft. For example, FIG. 32 discloses a flow divider 1410 deployed within an aorta B, and coupled to a deployment wire 1470 that is extended from a lumen with an opening in the distal end 1406 of the catheter shaft 1402. The flow divider 1410 is preferably comprised of a material or materials with a shape memory, so that the flow divider 1410 will assume the desired configuration on release from the catheter shaft 1402. Any known suitable materials may be used including, but not limited to, elastomers, thermoplastic elastomers, polyvinylchloride, polyurethane, polyethylene, polyamides, polyesters, silicone, latex, and alloys or copolymers, and reinforced composites thereof. In some embodiments, the flow divider 1410 may include lateral or branch stiffeners to assist the flow divider 1410 in maintaining a desired configuration or shape. Perfusion of the arch vessels in this embodiment, may be provided by another perfusion source, such as a second catheter. FIG. 33 is a cross section view of the flow divider 1410 of FIG. 32 taken transversely through the aorta B showing a preferred position of the flow divider 1410 within the aorta B.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An aortic catheter comprising:
   an elongated shaft;
   a cerebral embolic protection assembly mounted to said elongate shaft and positioned on said elongated shaft such that, when the aortic catheter is in an operative position, said cerebral protection assembly is positioned within a lumen of an aortic arch of a patient, said cerebral embolic protection assembly having an upper surface facing toward the aortic arch vessels, an inflatable portion, and a lower surface facing away from the aortic arch vessels, said cerebral embolic protection assembly being configured to allow blood flow to enter the cerebral circulation while excluding emboli from the cerebral circulation, wherein said cerebral embolic protection assembly is configured to partition the lumen of the aortic arch into a first fluid flow channel in fluid communication with the aortic arch vessels and a second fluid flow channel in fluid communication with the patient's corporeal circulation.

2. The aortic catheter of claim 1, wherein said cerebral embolic protection assembly is configured to allow blood flow to enter the first fluid flow channel in fluid communication with the aortic arch vessels while excluding emboli from entering the first fluid flow channel.

3. The aortic catheter of claim 1, wherein at least a portion of said cerebral embolic protection assembly is porous.

4. The aortic catheter of claim 3, wherein the porous portion of said cerebral embolic protection assembly is constructed of filter mesh that is permeable to blood and impermeable to emboli.

5. The aortic catheter of claim 3, wherein the porous portion of said cerebral embolic protection assembly is configured to allow blood flow to the cerebral circulation while excluding emboli from the cerebral circulation.

6. The aortic catheter of claim 3, wherein the porous portion of said cerebral embolic protection assembly is configured to exclude macroemboli from the cerebral circulation.

7. The aortic catheter of claim 3, wherein the porous portion of said cerebral embolic protection assembly is configured to exclude macroemboli and micro emboli from the cerebral circulation.

8. The aortic catheter of claim 3, wherein the porous portion of said cerebral embolic protection assembly is configured to divert emboli downstream to the patient's corporeal circulation.

9. The aortic catheter of claim 3, wherein the porous portion of said cerebral embolic protection assembly is configured to divert microemboli downstream to the patient's corporeal circulation and to capture macroemboli.

10. The aortic catheter of claim 1, wherein said cerebral embolic protection assembly is configured to exclude macroemboli from the cerebral circulation.

11. The aortic catheter of claim 1, wherein said cerebral embolic protection assembly is configured to exclude macroemboli and microemboli from the cerebral circulation.

12. The aortic catheter of claim 1, wherein said cerebral embolic protection assembly is configured to divert emboli downstream to the patient's corporeal circulation.

13. The aortic catheter of claim 1, wherein said cerebral embolic protection assembly is configured to divert microemboli downstream to the patient's corporeal circulation and to capture macroemboli.

14. The aortic catheter of claim 1, wherein said cerebral embolic protection assembly is actively deployable from a compressed condition wherein said cerebral embolic protection assembly is folded or compressed toward said elongate shaft and an expanded condition wherein said cerebral embolic protection assembly extends from said elongate shaft.

15. The aortic catheter of claim 1, wherein said cerebral embolic protection assembly comprises an upper portion comprised of impermeable material and a lower portion comprised of impermeable material.

16. The aortic catheter of claim 1, wherein said cerebral embolic protection assembly comprises an upper portion comprised of porous material and a lower portion comprised of porous material.

17. The aortic catheter of claim 1, further comprising a fluid lumen extending at least in part along the length of said elongated shaft and having a fluid port configured to provide fluid to the cerebral circulation.

18. The aortic catheter of claim 1 wherein said cerebral embolic protection assembly comprises an upper portion and a lower portion comprised of filter mesh.

19. The aortic catheter of claim 1, further comprises an auxiliary flow control member.

20. The aortic catheter of claim 19, wherein said auxiliary flow control member is in the form of an inflatable balloon.

21. The aortic catheter of claim 19, wherein said auxiliary flow control member is comprised of a peripheral flow control valve.

22. The aortic catheter of claim 1, wherein said elongated shaft is sized and configured to be inserted into a peripheral artery and navigated proximate the aortic arch.

23. The aortic catheter of claim 1, wherein said elongated shaft is sized and configured to be inserted directly into the aorta.

24. The aortic catheter of claim 1, wherein said elongated shaft is sized and configured to be inserted through an intercostal space.

25. An aortic catheter comprising:

an elongated shaft;

a cerebral embolic protection assembly mounted to said elongate shaft and positioned on said elongated shaft such that, when the aortic catheter is in an operative position, said cerebral protection assembly is positioned within a lumen of an aortic arch of a patient, said cerebral embolic protection assembly having an upper surface facing toward the aortic arch vessels, an inflatable portion, and a lower surface facing away from the aortic arch vessels, said cerebral embolic protection assembly being configured to allow blood flow to enter the cerebral circulation while excluding emboli from the cerebral circulation, wherein said cerebral embolic protection assembly is configured to partition the lumen of the aortic arch longitudinally into a first fluid flow channel in fluid communication with the aortic arch vessels and a second fluid flow channel in fluid communication with the patient's corporeal circulation, wherein at least a portion of said cerebral embolic protection assembly is porous and, wherein the porous portion of said cerebral embolic protection assembly is configured to allow blood flow to enter the first fluid flow channel from the second fluid flow channel, while excluding emboli from entering the first fluid flow channel from the second fluid flow channel.

26. An aortic catheter comprising:

an elongated shaft;

a cerebral embolic protection assembly mounted to said elongate shaft and positioned on said elongated shaft such that, when the aortic catheter is in an operative position, said cerebral protection assembly is positioned within a lumen of an aortic arch of a patient, said cerebral embolic protection assembly having an upper surface facing toward the aortic arch vessels, an inflatable portion, and a lower surface facing away from the aortic arch vessels, said cerebral embolic protection assembly being configured to allow blood flow to enter the cerebral circulation while excluding emboli from the cerebral circulation, wherein said cerebral embolic protection assembly is passively deployable from a compressed condition wherein said cerebral embolic protection assembly is folded or compressed toward said elongate shaft and an expanded condition wherein said cerebral embolic protection assembly extends from said elongate shaft.

27. A cerebral embolic protection assembly comprising:

a body having an upper surface, an inflatable portion, and a lower surface, said body being configured to be inserted in an operative position within a lumen of an aortic arch of a patient with said upper surface facing toward the aortic arch vessels and said lower surface facing away from the aortic arch vessels, said body being configured to allow blood flow to enter the cerebral circulation while excluding emboli from the cerebral circulation, wherein said body is configured to partition the lumen of the aortic arch longitudinally into a first fluid flow channel in fluid communication with the aortic arch vessels and a second fluid flow channel in fluid communication with the patient's corporeal circulation.

28. The cerebral embolic protection assembly of claim 27, wherein said body is configured to allow blood flow to enter the first fluid flow channel in fluid communication with the aortic arch vessels while excluding emboli from entering the first fluid lowflow channel.

29. The cerebral embolic protection assembly of claim 27, wherein at least a portion of said body is porous.

30. The cerebral embolic protection assembly of claim 27, wherein the porous portion of said body is constructed of filter mesh that is permeable to blood and impermeable to emboli.

31. The cerebral embolic protection assembly of claim 27, wherein the porous portion of said body is configured to allow blood flow to the cerebral circulation while excluding emboli from the cerebral circulation.

32. The cerebral embolic protection assembly of claim 27, wherein the porous portion of said body is configured to exclude macroemboli from the cerebral circulation.

33. The cerebral embolic protection assembly of claim 27, wherein the porous portion of said body is configured to exclude macroemboli and microemboli from the cerebral circulation.

34. The cerebral embolic protection assembly of claim 27, wherein the porous portion of said body is configured to divert emboli downstream to the patient's corporeal circulation.

35. The cerebral embolic protection assembly of claim 27, wherein the porous portion of said body is configured to divert microemboli downstream to the patient's corporeal circulation and to capture macroemboli.

36. The cerebral embolic protection assembly of claim 27, wherein at least a portion of said body is porous and, wherein the porous portion of said body is configured to allow blood flow to enter the first fluid flow channel from the second fluid flow channel, while excluding emboli from entering the first fluid flow channel from the second fluid flow channel.

37. The cerebral embolic protection assembly of claim 27, wherein said body is configured to exclude macroemboli from the cerebral circulation.

38. The cerebral embolic protection assembly of claim 27, wherein said body is configured to exclude macroemboli and microemboli from the cerebral circulation.

39. The cerebral embolic protection assembly of claim 27, wherein said body is configured to divert emboli downstream to the patient's corporeal circulation.

40. The cerebral embolic protection assembly of claim 27, wherein said body is configured to divert microemboli downstream to the patient's corporeal circulation and to capture macroemboli.

41. The cerebral embolic protection assembly of claim 27, wherein said body is foldable or compressible into compressed condition for insertion into the patient's aorta.

42. A method of cerebral embolic protection comprising:

inserting a cerebral embolic protection assembly into an operative position within a lumen of an aortic arch of a patient, and inflating at least a portion of said cerebral embolic protection assembly such that an upper surface of the cerebral embolic protection assembly faces toward the aortic arch vessels and a lower surface of the cerebral embolic protection assembly faces away from the aortic arch vessels, wherein the cerebral embolic protection assembly partitions the lumen of the aortic arch longitudinally into a first fluid flow channel in fluid communication with the aortic arch vessels and a second fluid flow channel in fluid communication with the patient's corporeal circulation, the cerebral embolic protection assembly allowing blood flow to enter the cerebral circulation while excluding emboli from the cerebral circulation.

43. The method of claim 42, wherein the cerebral embolic protection assembly diverts emboli downstream to the patient's corporeal circulation.

44. The method of claim 42, further comprising:

partitioning the lumen of the aortic arch with a filter material permeable to blood and impermeable to emboli.

45. The method of claim 44, wherein the filter material of the cerebral embolic protection assembly diverts emboli downstream to the patient's corporeal circulation.

46. The method of claim 44, wherein the filter material of the cerebral embolic protection assembly excludes macroemboli from the patient's cerebral circulation.

47. The method of claim 44, wherein the filter material of the cerebral embolic protection assembly diverts microemboli downstream to the patient's corporeal circulation and captures macroemboli within the filter material.

48. The method of claim 44, wherein the filter material of the cerebral embolic protection assembly excludes macroemboli and microemboli from the patient's cerebral circulation.

49. The method of claim 42, further comprising:

perfusing the patient's cerebral circulation through a lumen within the cerebral embolic protection assembly.

50. The method of claim 42, wherein the cerebral embolic protection assembly is inserted into the patient's aorta through a peripheral arterial access point.

51. The method of claim 42, wherein the cerebral embolic protection assembly is inserted directly into the patient's aorta through an incision in the aortic wall.

\* \* \* \* \*